(12) United States Patent
Hering et al.

(10) Patent No.: US 6,596,855 B2
(45) Date of Patent: Jul. 22, 2003

(54) PROBES FOR CHONDROGENESIS

(75) Inventors: Thomas M. Hering, Shaker Heights, OH (US); Brian Johnstone, Shaker Heights, OH (US)

(73) Assignee: Case Western Reserve University, Cleveland, OH (US)

(*) Notice: Subject to any disclaimer, the term of this patent is extended or adjusted under 35 U.S.C. 154(b) by 0 days.

(21) Appl. No.: 09/881,578

(22) Filed: Jun. 14, 2001

(65) Prior Publication Data

US 2003/0039966 A1 Feb. 27, 2003

Related U.S. Application Data

(60) Provisional application No. 60/211,384, filed on Jun. 14, 2000.

(51) Int. Cl.[7] ............................................. C12N 15/12
(52) U.S. Cl. ..................................................... 536/23.5
(58) Field of Search ........................................ 536/23.5

(56) References Cited

FOREIGN PATENT DOCUMENTS

WO         01/24833         4/2001

OTHER PUBLICATIONS

"Chondrocyte expressed protein–68 (CEP–68), a novel human marker gene for cultured chondrocytes" by Steck, et al., *Biochem. J.*, (2001) 353, 169–174.

"Chondrocyte–specific Enhancer Regions in the COMP Gene" by Issack, et al., *Journal of Orthopaedic Research*, 18:345–350, 2000.

"Mouse cathepsin K: cDNA cloning and predominant expression of the gene in osteoclasts, and in some hyertrophying chondrocytes during mouse development" by Rantakakko, et al., *FEBS Letters*, 393 (1996) 307–313.

"Cell Surface Antigens on Human Marrow–Derived Mesenchymal Cells Are Detected by Monoclonal Antibodies" by Haynesworth, et al., *Bone*, 13, 69–80 (1992).

"The Matrix Gla Protein Gene is a Marker of the Chondrogenesis Cell Lineage During Mouse Development" by Luo, et al., *Journal of Bone and Mineral Research*, vol. 10, No. 2, 1995, 325–334.

"Chondrogenesis in Periosteal Explants" by O'Driscoll, et al., *The Journal of Bone and Joint Surgery*, 1994, pp. 1042–1051.

"Novel Zinc–Finger Proteins Expressed During In Vitro Chondrogenesis" by Hering, et al., 47th Annual Meeting, Orthopaedic Research Society, Feb. 25–28, 2001, San Francisco, California.

"Novel Zinc–Finger Proteins Expressed by Mesenchymal Progenitor Cells During In Vitro Chondrogenesis" by Hering, et al., First Symposium of the International Society for Matrix Biology, Jun. 14–17, 2000, Jefferson Medical College, Philadelphia, Pennsylvania.

Abstract G130. "Novel Zinc–Finger Proteins CZF–1 and CZF–2 Expressed During Chondrogenesis" by Hering, et al., International Coference on Biology and Pathology of the Extracellular Matrix, Oct. 12–15, 2000, Washington University Medical Center, St. Louis, Missouri.

GenBank Accession No. BE682165 dated Apr. 25, 2001.

GenBank Accession No. AC007228 dated Apr. 6, 1999.

*Primary Examiner*—Terry McKelvey
(74) *Attorney, Agent, or Firm*—Calfee, Halter & Griswold LLP

(57) ABSTRACT

Markers for detecting and staging chondrogenesis in cells are provided. In one aspect the markers are isolated polynucleotides, referred to hereinafter as CZF-1 and CZF-2, and fragments thereof. In one embodiment, the CZF-1 polynucleotide comprises the open reading frame sequence set forth in SEQ ID NO.1. In one embodiment, the CZF-2 polynucleotide comprises the open reading frame sequence set forth in SEQ ID NO. 3. In another aspect the markers are antibodies, which are immunospecific for proteins encoded by CZF-1 or CZF-2. Methods which employ the present markers to identify cells that have begun to differentiate into chondrocytes are provided. The present invention also relates to the CZ-1 protein and the CZ-2 protein and to polynucleotides or oligonucleotides whose sequences are complementary to the coding sequences of CZF-1 or CZF-2, or regions thereof.

6 Claims, 15 Drawing Sheets

(1 of 15 Drawing Sheet(s) Filed in Color)

Fig. 2

CHONDROGENIC LINEAGE

STEM CELL
↓
COMMITTED Chondroprogenitor : Type I Collagen
↓
Chondrogenic PROGENITOR : Type VI Collagen, CSPG-M
↓
Chondroblast : Type II Collagen, CDI(28Kd), CSPG-H (aggrecan)
↓
Chondrocyte I : 148Kd, link, protein
↓
Chondrocyte II : 100 Kd, matric, vesicle production
↓
Hypertrophic Chondrocyte : Type X Collagen, 59Kd, $1,25\text{-}(OH)_2D_3R$
↓
Calcifying Chondrocyte : Type I Collagen, 63Kd, osteopontin, osteocalin, steonectin

Fig. 3A

Sequence of CZF-1 (cDNA)

```
                                                 50
AATGGAGCGAAGACCATGGGGACTGAGTACACAGATGAAGACACAGAAGC

100
ATAGAGAGGATAAGTAATCACTAGCAAGTGGAAGAACCGGGATTCAGATC

150
CAGAACAGGCTGACTCCAGAGTCACTGGCTGTCATGTAGTTTCCTCAACT

200
ACTGCCTCAGCTCTACAATCCCAGAGTAAAGCTCTTCTCCAAATGAAGAG

250
CCAGGAAGAGGTAGAGGTGGCAGGAATTAAACTTTGTAAAGCCATGTCCC

300
TGGGTTCACTGACTTTCACAGATGTGGCCATAGACTTTTCCCAAGATGAA

350
TGGGAGTGGCTGAATCTTGCTCAGAGAAGTTTGTACAAGAAGGTGATGTT

400
AGAAAACTACAGGAACCTAGTTTCAGTGGGTCTTTGCATTTCTAAACCAG

450
ATGTGATCTCCTTACTGGAGCAAGAGAAAGACCCTTGGGTGATAAAAGGA

500
GGGATGAACAGAGGCCTGTGCCCAGACTTGGAGTGTGTGTGGGTGACCAA

550
ATCATTATCTTTAAACCAGGATATTTATGAAGAAAATTACCCCCGGCAA

600
TCATAATGGAAAGACTTAAAAGCTATGACCTTGAATGTTCAACATTAGGG

650
AAAAACTGGAAATGTGAAGACTTGTTTGAGAGGGAGCTTGTAAACCAGAA

700
GACACATTTTAGGCAAGAGACCATCACTCATATAGATACTCTTATTGAAA

750
AAAGAGATCACTCTAACAAATCTGGGACAGTTTTTCATCTGAATACATTA

800
TCTTATATAAAACAGATTTTTCCCATGGAAGAGAGAATATTTAATTTTCA
```

Fig. 3B

```
                                            850
TACAGATAAGAAAAGCTTAAAAACACATTCAGTTGTGAAAAAACACAAGC

900
AAGACCGTGGAGAAAAGAAACTTTTAAAATGTAATGACTGTGAGAAAATA

950
TTCAGCAAAATCTCAACCCTTACTCTTCACCAAAGAATTCATACAGGAGA

1000
GAAACCCTATGAATGTATTGAATGTGGAAAGGCCTTTAGCCAGAGTGCCC

1050
ACCTTGCTCAACATCAGAGAATACACACAGGAGAAAAACCTTTTGAATGT

1100
ACTGAATGTGGGAAAGCCTTCAGCCAGAATGCTCATCTTGTTCAACACCA

1150
GAGAGTTCATACTGGAGAGAAACCTTATCAGTGTAAGCAGTGTAATAAAG

1200
CATTCAGCCAGCTTGCACACCTTGCTCAACATCAGAGGGTCCACACTGGA

1250
GAGAAACCCTATGAATGTATTGAATGTGGGAAGGCTTTTAGTGATTGCTC

1300
ATCCCTAGCTCATCATCGAAGGATTCACACTGGGAAAGACCTTATGAAT

1350
GTATTGACTGTGGGAAAGCTTTCAGGCAGAATGCTTCTCTTATACGTCAT

1400
CGGCGATATTATCATACTGGAGAGAAACCCTTTGACTGTATTGATTGTGG

1450
GAAGGCTTTCACTGATCACATAGGACTTATTCAGCATAAGAGAATTCATA

1500
CTGGAGAGAGACCTTACAAATGTAATGTGTGTGGGAAGGCTTTTAGCCAT

1550
GGCTCATCTCTGACAGTACATCAGAGAATTCATACAGGAGAGAAACCTTA

1600
TGAATGCAATATCTGTGAGAAAGCCTTCAGCCATCGTGGGTCTCTTACTC
```

Fig. 3C

```
                                               1650
TTCATCAGAGAGTTCATACTGGAGAGAAACCCTATGAATGTAAAGAATGT

1700
GGGAAAGCTTTCCGGCAGAGCACGCATCTGGCTCATCATCAGAGAATTCA

1750
TACTGGAGAGAAACCTTATGAATGTAAGGAATGCAGCAAAACCTTCAGCC

1800
AGAATGCACACCTCGCGCAGCATCAGAAAATACACACTGGGGAGAAGCCT

1850
TATGAATGTAAGGAACGTGGTAAGGCCTTCAGTCAGATTGCACACCTTGT

1900
TCAGCACCAGAGAGTTCATACTGGTGAGAAGCCTTACGAATGTATTGAAT

1950
GTGGGAAGGCCTTTAGTGATGGCTCATATCTTGTTCAACATCCGAGACTC

2000
CACAGTGGCAAAAGACCGTATGAATGTCTTGAATGTGGGAAGGCATTCAG

2050
GCAGAGGGCATCCTTGATTTGTCATCAGAGATGTCATACTGGTGAGAAAC

2100
CTTATGAATGTAATGTTTGTGGGAAAGCCTTTAGCCATCGTAAATCCCTT

2150
ACTCTGCATCAGAGAATTCATACAGGAGAGAAACCTTATGAGTGTAAGGA

2200
ATGTAGCAAAGCCTTCAGCCAGGTTGCCCATCTTACTCTACATAAGAGAA

2250
TTCATACTGGAGAAAGGCCCTATGAGTGTAAAGAATGTGGAAAAGCCTTC

2300
AGGCAGAGTGTACATCTTGCTCATCATCAGCGAATTCATACCGGAGAGTC

2350
ATCAGTTATTCTCTCCTCTGCCCTCCCATACCACCAAGTCCTATAGATTC

2400
AATCTCGTAAATGCTTCTAGCATCCATCTGCTTTTTTCCAGCACATGTCC
```

Fig. 3D

```
                                               2450
CATCATCATAGTCCAAGACGCAACCATCTCATCTGGATTTCTGCAGTAGC

2500
ATAACTGTTGCCCCTTTTGCTTCTATCAACTACATGTTTAACACTGTAGG

2550
CAGCCTAACCTTTTAAAATAAAAATACATAATTTATGTTATTTTCCCAT

2600
TTAAAACACTTGATTTGAAAATATATTAACTAATCCATTTCAAGGATTT

2650
AGCACACACTGGCATATAGTTATTGCTAAATAAATGCTAGCCATTAAGGT

2666
AAAAAAAAAAAAAAAA
```

```
                    KRAB-A                                          KRAB-B
MKSQEEVEVAGIKLCKAMSL|GSLTFTDVAIDFSQDEWEWLNLAQRSLYKKVMLENYRNLVSV|GLCISKPDVISLLEQ

|EKDPWVIKGGMNRGLCP|DLECVWVTKSLSLNQDIYEEKLPPAIIMERLKSYDLECSTLGKNWKCEDLFERELVNQKT

HFRQETITHIDTLIEKRDHSNKSGTVFHLNTLSYIKQIFPMEERIFNFHTDKKSLKTHSVVKKHKQDRGEKKLLKCN
ZF-1                       ZF-2                            ZF-3
DCEKIFSKISTLTLHQRIHTGEKPYECIECGKAFSQSAHLAQHQRIHTGEKPFECTECGKAFSQNAHLVQHQRVHTG
        ZF-4                      ZF-5                           ZF-6
EKPYQCKQCNKAFSQLAHLAQHQRVHTGEKPYECIECGKAFSDCSSLAHHRRIHTGKRPYECIDCGKAFRQNASLIR
           ZF-7                       ZF-8                           ZF-9
HRRYYHTGEKPFDCIDCGKAFTDHIGLIQHKRIHTGERPYKCNVCGKAFSHGSSLTVHQRIHTGEKPYECNICEKAF
                   ZF-10                      ZF-11
SHRGSLTLHQRVHTGEKPYECKECGKAFRQSTHLAHHQRIHTGEKPYECKECSKTFSQNAHLAQHQKIHTGEKPYEC
ZF-12                   ZF-13                         ZF-14
KERGKAFSQIAHLVQHQRVHTGEKPYECIECGKAFSDGSYLVQHPRLHSGKRPYECLECGKAFRQRASLICHQRCHT
     ZF-15                     ZF-16                          ZF-17
GEKPYECNVCGKAFSHRKSLTLHQRIHTGEKPYECKECSKAFSQVAHLTLHKRIHTGERPYECKECGKAFRQSVHLA

HHQRIHTGESSVILSSALPYHQVL*
```

Fig. 4

```
     KRAB-A
MTD|GLVTFRDVAIDFSQEEWECLDPAQRDLYVDVMLENYSNLVSL|DLESKTYETKKIFSENDIFEINFSQWEMK
                                                                          ZF-1
DKSKTLGLEASIFRNNWKCKSIFEGLKGHQEGYFSQMIISYEKIPSYRKSKSLTPHQRIHNTEKSYVCKECGK
              ZF-2                      ZF-3
ACSHGSKLVQHERTHTAEKHFECKECGKNYLSAYQLNVHQRFHTGEKPYECKECGKTFSWGSSLVKHERIHT
      ZF-4                    ZF-5                          ZF-6
GEKPYECKECGKAFSRGYHLTQHQKIHIGVKSYKCKECGKAFFWGSSLAKHEIIHTGEKPYKCKECGKAFSR
           ZF-7                    ZF-8
GYQLTQHQKIHTGKKPYECKICGKAFCWGYQLTRHQIFHTGEKPYECKECGKAFNCGSSLIQHERIHTGEKP
      ZF-9                     ZF-10                        ZF-11
YECKECGKAFSRGYHLSQHQKIHTGEKPFECKECGKAFSWGSSLVKHERVHTGEKSHECKECGKTFCSGYQLT
         ZF-12
RHQVFHTGEKPYECKECGKAFNCGSSLVQHERIHTGEKPYECKECGRLLVVAITLLNIRKFIPVRNLSNVRNV

GRPSVGVQA*
```

Sequence of CZF-2 (cDNA)

```
                                                           50
GGGAGTTCTTGCAATTCCAGAACCATGACTGATGGGTTGGTGACATTCAG

100
GGATGTGGCCATCGACTTCTCTCAGGAGGAGTGGGAATGCCTGGACCCTG

150
CTCAGAGGGACTTGTACGTGGATGTAATGTTGGAGAACTATAGTAACTTG

200
GTGTCACTGGATTTGGAGTCAAAAACGTATGAGACCAAAAAATATTTTTC

250
AGAAAATGATATTTTTGAAATAAATTTTTCCCAGTGGGAGATGAAGGACA

300
AAAGTAAAACCCTTGGCCTTGAGGCATCCATCTTCAGAAATAATTGGAAG

350
TGCAAAAGCATATTCGAGGGACTAAAAGGACATCAAGAGGGATACTTCAG

400
TCAAATGATAATCAGCTATGAAAAAATACCTTCTTACAGAAAAGTAAAT

450
CTCTTACTCCACATCAAAGAATTCATAATACAGAGAAATCCTATGTTTGT

500
AAGGAATGTGGGAAGGCTTGCAGTCATGGCTCAAAACTTGTTCAACATGA

550
GAGAACTCATACAGCTGAAAAGCACTTTGAATGTAAAGAATGTGGGAAGA

600
ATTATTTAAGTGCCTATCAACTCAATGTGCATCAGAGATTTCATACTGGT

650
GAGAAACCCTATGAGTGTAAGGAATGTGGGAAGACCTTTAGCTGGGGATC

700
AAGCCTTGTTAAACATGAGAGAATTCACACTGGTGAGAAACCCTATGAAT

750
GTAAAGAATGTGGGAAGGCCTTTAGTCGTGGCTATCACCTTACCCAACAT

800
CAGAAAATTCATATTGGTGTGAAATCTTATAAATGTAAGGAATGTGGGAA
```

Fig. 5B

```
                                               850
GGCCTTTTTTTGGGGCTCAAGCCTTGCTAAACATGAGATAATTCATACAG

900
GTGAGAAACCTTATAAATGTAAAGAATGTGGGAAGGCCTTCAGTCGTGGC

950
TATCAACTTACTCAGCATCAGAAAATCCATACTGGTAAGAAACCTTATGA

1000
ATGTAAAATATGTGGAAAGGCTTTTTGTTGGGGCTATCAACTTACTCGAC

1050
ATCAGATATTTCATACTGGTGAGAAACCCTATGAATGCAAGGAATGTGGG

1100
AAGGCTTTTAATTGCGGATCAAGTCTTATTCAACATGAAAGAATTCATAC

1150
TGGTGAGAAACCTTATGAATGTAAAGAATGTGGAAAGGCCTTTAGTCGTG

1200
GCTATCACCTTTCTCAACATCAGAAAATCCATACTGGTGAGAAACCTTTT

1250
GAATGTAAGGAATGTGGGAAGGCCTTTAGTTGGGGTTCAAGCCTTGTTAA

1300
ACATGAGAGAGTTCATACTGGTGAGAAATCCCATGAATGTAAAGAATGCG

1350
GAAAGACCTTTTGTAGTGGGTATCAACTTACTCGACATCAGGTATTTCAC

1400
ACTGGTGAGAAACCCTATGAATGTAAGGAATGTGGGAAGGCTTTTAATTG

1450
TGGATCAAGCCTTGTTCAACATGAAAGAATCCATACAGGGGAGAAACCCT

1500
ATGAATGTAAAGAATGTGGAAGGCTTTTAGTCGTGGCTATCACCTTACTC

1550
AACATCAGAAAATTCATACCGGTGAGAAACCTTTCAAATGTAAGGAATGT

1600
GGGAAGGCCTTCAGTTGGGGTTCAAGCCTAGTTAAGCATGAGAGAGTCCA
```

Fig. 5C

```
                                              1650
TACTAATGAGAAGTCTTATGAATGTAAAGACTGTGGGAAGGCCTTTGGTA

1700
GTGGCTATCAACTTAGTGTTCATCAGAGATTTCATACTGGTGAGAAGCTT

1750
TATCAACATAAGGAATTCGGGAAGACCTTTACTCGTGGCTCAAAACTTGT

1800
TCATGAGAGAACTCATAGTAATGATAAACCCTACAAATATAACGAATGTG

1850
GGGAAGCCTTTCTGTGGACAACTTACTCAAATGAGAAAATTGATACTGAT

1900
GAAACCTTATGATTGAAAGTTGTAAAAGAATATTTTGTGTGTGCGTATAG

1950
ACAACTTATCATAATAAGAACTCTTACTCTTGAGAAACCTTGTGAATGTA

2000
AGGGTTGTGCAAAAGCCATTCATTTCTGTTTATGGGCAATTATCTTGCTA

2050
TCCAGCAATTCATACTAGTGAGAAATATTTTGAATATAATTAATATGAAA

2100
AGGCCTTTAGACTTCTGTACAGTCTTATTGGATATCAATTTATACTGATG

2143
TAAAATCATTTAAATGAAAAAAAAAAAAAAAAAAAAAAAAA
```

PROBES FOR CHONDROGENESIS

This application claims priority to U.S. provisional application No. 60/211,384, filed Jun. 14, 2000.

This invention is supported, at least in part, by Grant Nos. RO1AR046196 and P60AR020618 from the National Institutes of Health. The Federal Government has certain rights in this invention.

FIELD OF THE INVENTION

This invention relates to probes for detecting chondrogenesis.

BACKGROUND

Cartilage is a dense connective tissue that comprises part of the skeleton in adult humans. Cartilage provides support and attachment points for body structures, protects underlying tissues, and provides structural models in which many bones develop.

Cartilage is largely comprised of cells, called chondrocytes, embedded in an extracellular matrix. The extracellular matrix mainly consists of collagen type II and proteoglycans, the components of which are exuded into the intercellular space by the chondrocytes, where they are assembled to form macromolecules. The chondrocytes make up about 5% of the volume of the cartilage tissue of an adult individual.

Chondrocytes are formed by differentiation of mesenchymal progenitor cells (MPCs), also called mesenchymal stem cells (MSCs). These cells form chondrocytes during embryonic development (see below). In addition, MPCs are found in many tissues of the adult body, and are multipotent in that they can differentiate into a number of different cell types (see FIG. 1). The process of differentiation from progenitor or stem cell to chondrocyte is called chondrogenesis.

Chondrogenesis in Development and Growth

Chondrocytes are an essential component to bone development and growth, a process called endochondral ossification. For example, most bones of the human skeleton develop from masses of hyaline cartilage. This cartilage is formed by chondrocytes that are differentiated from MPCs. The first part of chondrogenesis is the formation of a precartilage condensation, where the MPCs come together through cell-cell interactions and there is some proliferation. After condensation, the progression phase of chondrogenesis occurs, with cells beginning to produce molecules characteristic of cartilage, such as type II collagen. There is expansion of the cartilaginous tissue by production of large amounts of extracellular matrix containing mainly collagen and proteoglycans. This leads to the formation of a cartilage anlagen for a given bone.

In certain regions of this cartilage, the chondrocytes further differentiate into hypertrophic chondrocytes that secrete bone-related molecules and their surrounding extracellular matrix is calcified. The cells then die by apoptosis (programmed cell death). Blood vessels invade the calcified cartilage and osteoblasts (the cells responsible for bone formation) are attracted. Chondroclastic cells remove the cartilage and the osteoblasts lay down new bone. This bone is later remodeled by osteoclasts and osteoblasts to form mature bone.

Other regions of the cartilage anlagen are not removed during development; specifically the growth plates and the articular cartilages. Growth plate chondrocytes enter a programmed pathway in which they proliferate for some time and then become hypertrophic and die, with replacement of the hypertrophic region by the mechanism described above, involving blood vessel invasion, etc. This mechanism allows bones to grow longitudinally until puberty. Articular cartilage resembles the growth plate in the neonatal stage, but eventually there is formation of a cartilage in which the chondrocytes no longer proliferate or hypertrophy—a permanent cartilage. Articular cartilage is responsible for weight-bearing and shock absorption in joints. It is the cartilage that breaks down in degenerative arthritic diseases. Other permanent cartilages include those that form rings in the trachea or the cartilage of the nose and ears.

Because it is important, in certain instances, to monitor progression of chondrogenesis in both formation of cartilage and bone, there is a need for markers and probes to detect and ascertain the extent of these processes.

Chondrogenesis in Natural Repair and Regeneration

In addition to formation of bone during development, chondrocytes are also involved in the formation of bone in repair of bone fractures. Within a typical fracture site, there is both intramembranous bone formation (where there is no cartilage intermediate) and endochondral bone formation (in which cartilage is first formed and then replaced by bone, in a manner similar to that seen in development).

Immediately after a fracture, a fibrous clot is formed and granulation tissue results as macrophages and other cells invade it. This is called the "external callus." Bone begins to be made by osteoblasts adjacent to the fracture, forming a hard callus. At the same time, progenitor cells from the surrounding tissues proliferate and begin to differentiate into chondrocytes within the granulation tissue. This cartilaginous callus is later replaced by bone tissue, similar to the process in which hyaline cartilage of a developing bone is replaced.

Because the endochondral component is important to effect proper bone repair, there is a need for markers and probes to detect and ascertain the extent of chondrogenesis in this process. This is especially true when a so-called non-union occurs, in which the fracture does not heal. Understanding what stage the repair has reached would aid in the choice of the remedial treatment.

Chondrogenesis in Therapeutic Cartilage Repair and Regeneration

In a separate application, the use of implanted mesenchymal progenitor cells to produce repair of cartilaginous tissues would benefit from knowledge of the stage of differentiation that the cells have reached. For example, in articular cartilage repair, the undifferentiated progenitor cells, either injected or implanted into area of the body where there is defective cartilage, is a possible treatment modality. The course of such treatment includes the sampling (biopsy) of repair tissue at some time after implantation. In order to aid in decisions regarding the treatment, it is important to know the stage of chondrogenic differentiation that the implanted cells have reached. Thus, there is a need for markers and probes of chondrogenesis to detect and ascertain the extent of this process.

Chondrogenesis in vitro

In addition to the involvement of chondrocytes in natural body process, manipulation of chondrocytic precursors in vitro is becoming increasingly important for "tissue engineering" methodologies.

For example, a population of MPCs can be manipulated in vitro such that a majority of cells become chondrocytes (see U.S. Pat. No. 5,908,784 by Johnstone et al.). One use of such systems is to correct and repair cartilage defects through implantation into humans of such chondrocytes derived from differentiation of MPCs in vitro (for example, see U.S. Pat. No. 6,242,247 by Rieser, et al.).

Because tissue-engineered cartilage is a possible treatment for cartilaginous defects, there is a need for probes and detection methods to ensure that mesenchymal cells have differentiated into chondrocytes during the in vitro production of the cartilage.

Differentiation of MPCs as Related to Cancer

Chondrosarcoma is the second most common form of bone malignancy. These are generally slow growing sarcomas that are of unknown etiology and the cell type that initiates the formation of a chondrosarcoma within a bone is not known. Such cells, however, are characterized by the production of cartilage within the sarcoma by cells that differentiate into chondrocyte-like cells. In a specific type of chondrosarcoma, called "mesenchymal chondrosarcoma," cells of the tumor comprised all differentiation stages between and including MPCs and hypertrophic chondrocytes (Aigner, et al., 2000, Am J Pathol, 156:1327–35.).

Conventional chondrosarcoma tumors are graded from stage I through stage III, stage III being the most advanced. Such grading of chondrosarcomas is important for proper diagnosis and treatment of the condition. However, diagnosis and grading of chondrosarcoma has been problematic. For example, the criteria used to distinguish benign enchondroma from low grade chondrosarcoma include parameters which are difficult to quantify such as increased cellularity and more than occasional binucleate cells. These histologic criteria are not absolute, and the diagnosis is frequently made by taking into account clinical features such as pain, rate of growth, location, and radiologic features.

Because it is difficult to stage these sarcomas, there is a need for probes and better detection methods to aid in the definition of the grade of a given chondrosarcoma to assist in the decision-making process for treatment.

SUMMARY OF THE INVENTION

The present invention provides new markers which can be used for detecting and staging chondrogenesis in cells. In one aspect, the markers are isolated polynucleotides, referred to hereinafter as CZF-1 and CZF-2, and fragments thereof. In one embodiment, the CZF-1 polynucleotide comprises the sequence set forth in SEQ ID NO. 1. In one embodiment, the CZF-2 polynucleotide comprises the sequence set forth in SEQ ID NO. 3. In another aspect the markers are antibodies which are immunospecific for the proteins encoded by CZF-1 or CZF-2.

The present invention also provides methods which employ the present markers to identify cells that have begun to differentiate into chondrocytes. Such cells are referred to hereinafter as "cells of interest". In one aspect, the method involves contacting the CZF-1 polynucleotide or a fragment thereof, or the CZF-2 polynucleotide or a fragment thereof, with RNA that has been extracted from or, alternatively, contained within the cells of interest, and assaying for the presence of a hybridization product between the polynucleotide and the RNA. In another aspect, the RNA is reverse transcribed and amplified using primers that have been derived from the CZF-1 or CZF-2 polynucleotides. In a further aspect, the method comprises contacting the cells of interest with antibodies that are immunospecific for the CZF-1 protein or the CZF-2 protein and assaying for the formation of an antigen-antibody complex between the anti-CZF-1 or anti-CZF-2 antibody and a protein in the cell.

The present invention also relates to the CZF-1 protein and the CZF-2 protein. Such proteins are useful for preparing antibodies that are used in the present methods for characterizing cells. The present invention also relates to polynucleotides or oligonucleotides whose sequences are complementary to the coding sequences of CZF-1 or CZF-2, or regions thereof. Such polynucleotides and oligonucleotides are useful as probes or primers.

DESCRIPTION OF THE FIGURES

The file of this patent contains at least one drawing executed in color.

The present invention may be more readily understood by reference to the following figures wherein:

FIG. 2 is a diagram of differentiation of MPCs into chondrocytes; and

FIGS. 3A–3D are the DNA sequence of the full-length CZF-1 gene (SEQ ID NO. 1); and FIG. 4 is the predicted amino acid sequence of the CZF-1 protein (SEQ ID NO. 2); and FIGS. 5A–5C are the DNA sequence of the full-length CZF-2 gene (SEQ ID NO. 3); and FIG. 6 is the predicted amino acid sequence of the CZF-2 protein (SEQ LD NO. 4)

DETAILED DESCRIPTION OF THE INVENTION

Definitions

Figure 1:
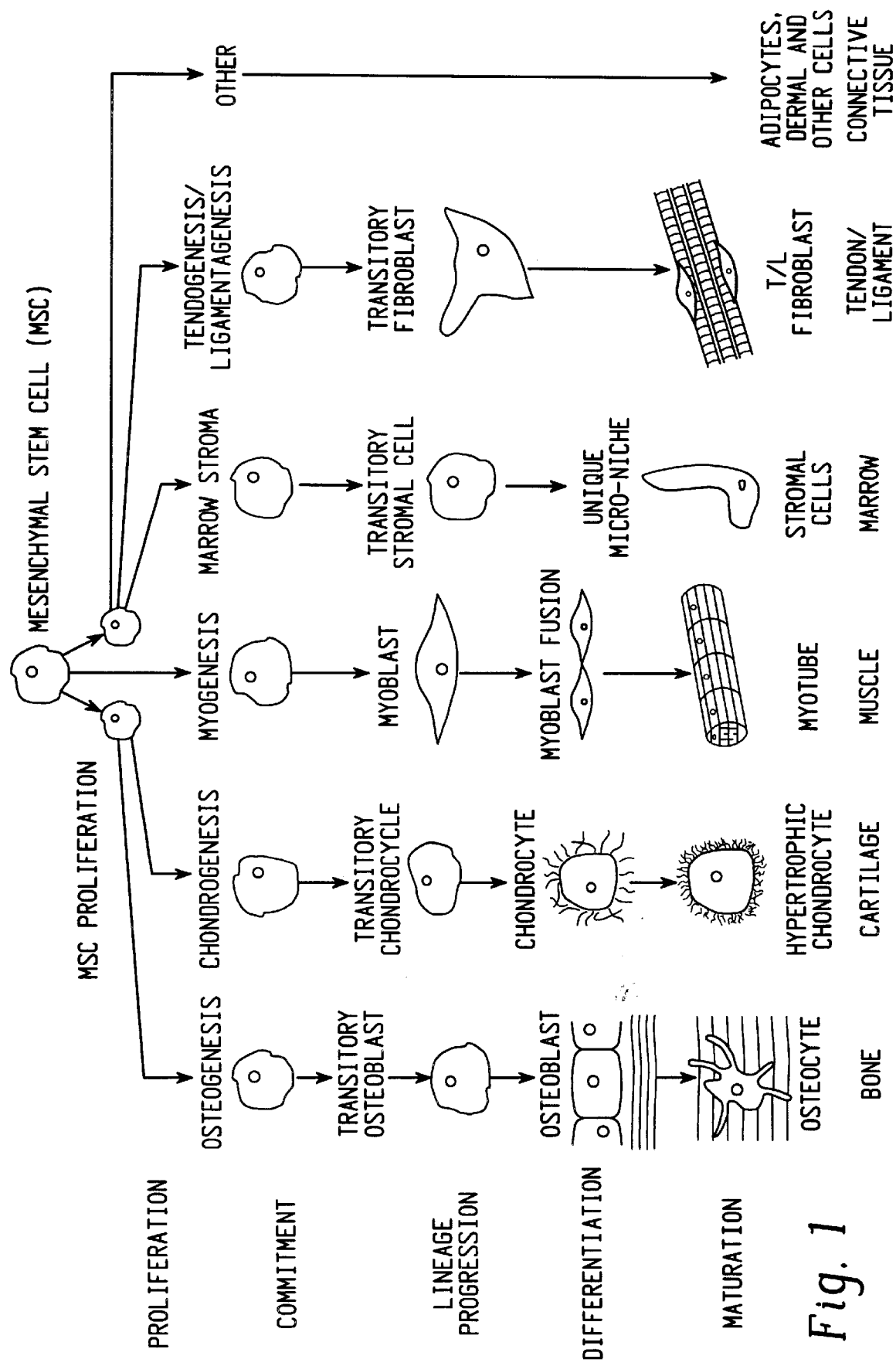
FIG. 1 is a diagram of MPC differentiation along different cell lineages.
Figure 7:
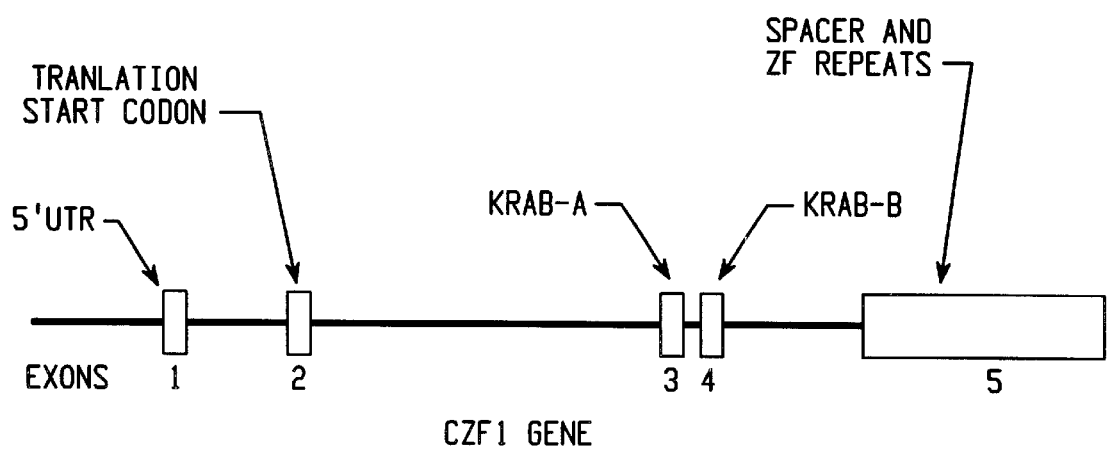
FIG. 7 is a diagram of the structure of the CZF-1 gene.

Unless otherwise indicated, the following terms used in this document have the following meanings:

"Transcription factor" refers to a protein that interacts, either directly or indirectly through other proteins, with RNA polymerase II to initiate transcription. Some transcription factors have the ability to bind to specific nucleotide sequences within DNA.

"Zinc-finger" refers to one or more motifs within a protein that bind to Zn2+, such binding causing arrangement of the motif such that an a-helix within the motif can fit into and bind to the major groove of the DNA.

"Mesenchymal cells" refers to cells that can differentiate into a variety of differentiated cell types, including bone, bone marrow, cartilage, muscle, tendons and ligaments, and connective tissues.

"Chondrocytes" refers to cells that comprise cartilage.

"Chondrogenesis" refers to formation of cartilage, more specifically, to formation of chondrocytes from mesenchymal progenitor cells.

The present invention relates to isolated polynucleotides and oligonucleotides that are useful for characterizing the extent of chondrogenesis in cells of interest. In accordance with the present invention, the polynucleotides and oligonucleotides are derived from two genes, CZF-1 and CZF-2, that are transiently expressed during the early stages of chondrogenesis.

Discovery and Isolation of CZF Genes

A cell culture system that facilitates chondrogenic differentiation of postnatal mammalian marrow mesenchymal progenitor cells (MPCs), in a defined medium that includes dexmathasone and TGFβ-1, was the source of RNA that was used for isolation of CZF-1 and -2 cDNAs (Johnstone, et al., 1998, Exp Cell Res, 238:265–72 and U.S. Pat. No. 5,908,784).

In this in vitro differentiation system, MPCs progress through a number of stages which are defined by expression of various markers (see FIG. 2). Expression of collagen type II is a marker of chondrocytes and its expression begins to be seen after the cells of this system are in culture for 4 days. Collagen expression levels continue to increase thereafter. In this system, the cells continue to differentiate to form hypertrophic chondrocytes, which are marked by expression of collagen type X. Collagen type X expression begins to occur on day 6, but doesn't reach high levels until after day 7.

RNA was prepared from the cells after 3 days in culture and is used to construct a cDNA library in the vector λgt10. This cDNA library was screened using a $^{32}$P-labeled degenerate oligonucleotide probe containing all possible permutations coding for the sequence of amino acids, HTGEKP (SEQ ID NO. 6).

The HTGEKP sequence (SEQ ID NO. 6) is a sequence motif common to proteins of the class called "zinc-finger" proteins. Such zinc-finger proteins have the ability to bind to DNA and these proteins have been shown to be transcription factors. Zinc-finger transcription factors of the $Cys_2His_2$ (SEQ ID. NO. 7) type are characterized by tandem arrays of sequence conforming approximately to the motif (Tyr, Phe)-X-Cys-$X_{2-4}$-Cys-$X_3$-Phe-$X_5$-Leu-$X_2$-His-$X_{3-5}$-His, (SEQ ID NOS. 8–13) where X represents any essential amino acid. The linker that connects adjacent zinc-finger domains is well conserved and has the consensus sequence His-Thr-Gly-Glu-Lys-Pro (HTGEKP) (SEQ ID NO. 6). Therefore, a degenerate oligonucleotide probe representative of all possible codons encoding HTGEKP (SEQ ID NO. 6) will hybridize to cDNA clones within the library encoding zinc-finger motifs.

Approximately 60,000 λ plaques were screened and plaques hybridizing to the degenerate HTGEKP (SEQ ID NO. 6) probe were obtained. The cDNA inserts of these hybridizing clones were amplified using the polymerase chain reaction (PCR), cloned by the TA-tailing method, and the DNA sequence of the inserts was obtained. The obtained DNA sequences were compared to the NCBI nucleotide sequence database using the BLAST algorithm. The BLAST search showed that the one of the inserts (called CZF-1; Cartilage Zinc Finger) matched a 717 amino acid open reading frame (ORF) encoding a protein containing approximately 16 zinc-finger domains, within a 3.6 Mb region in 19q13.4. Additional sequence encoding the amino acid terminal region of the protein is obtained by performing a 5' RACE procedure. The final protein sequence was found to be 717 amino acid residues in length.

The BLAST search showed that the other insert (called CZF-2) contained a 518 amino acid ORF containing approximately 12 zinc-finger domains.

Characterization of CZF Gene Expression

Figure 8:
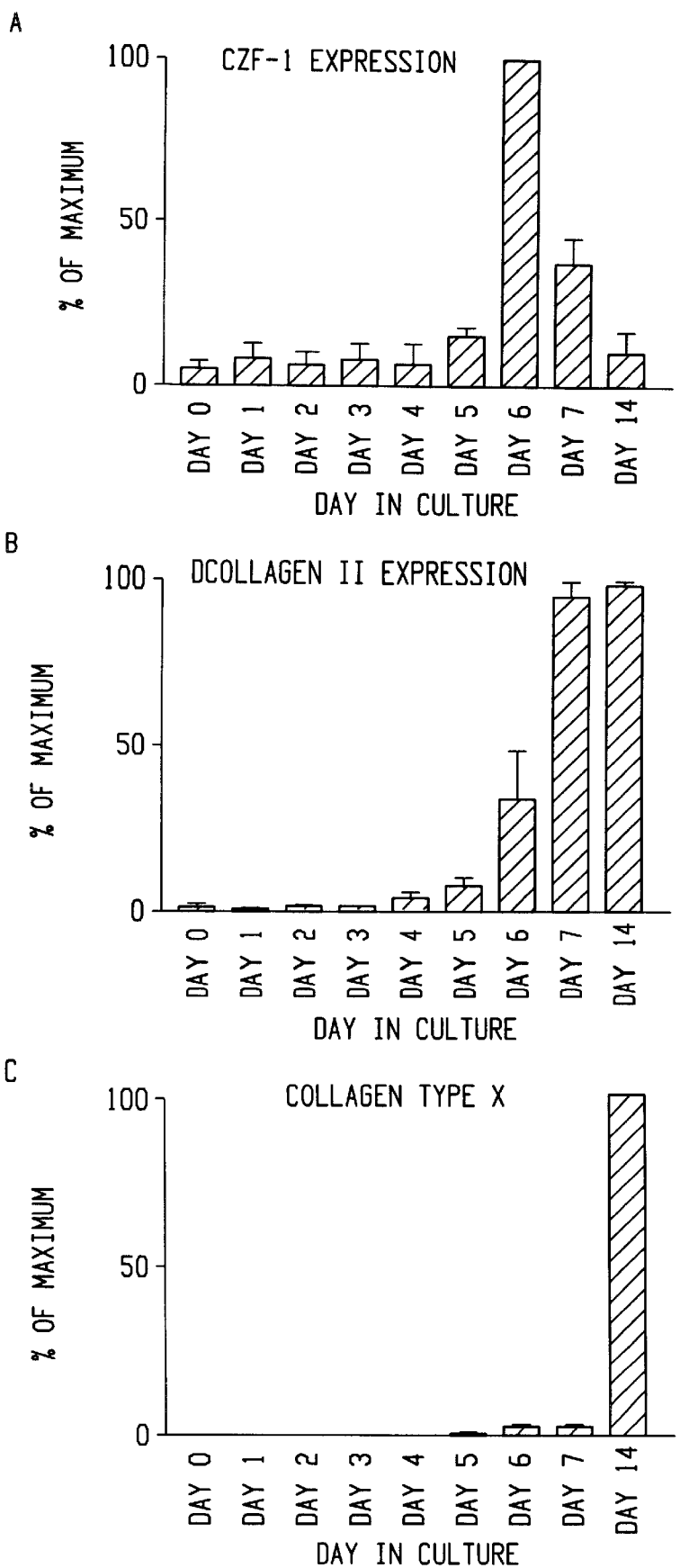
FIGS. 8A–8C contain charts of expression of CZF-1, collagen type II and collagen type X in MPCs undergoing chondrogenesis.

As stated earlier, in the in vitro system for differentiation of MPCs to chondrocytes, differentiation begins to occur after approximately 3 days in culture. This is shown in FIG. 8, which is RT-PCR amplification of CZF-1, collagen type II and collagen type X RNAs isolated differentiating MPCs on the days indicated. As indicated in FIG. 8, collagen type II begins to be expressed at around day 5 and is a marker of chondrocytes. In this system, the cells further differentiate to "hypertrophic" chondrocytes, as indicated by expression of collagen type X, which is not present at significant levels until after 7 days in this system.

In this cell system, CZF-1 expression begins on day 4–5 in culture, is maximal on day 6, and begins to decrease thereafter. Therefore, CZF-1 begins to be expressed earlier than does collagen type II and is a marker for formation of chondrocytes.

Figure 9:
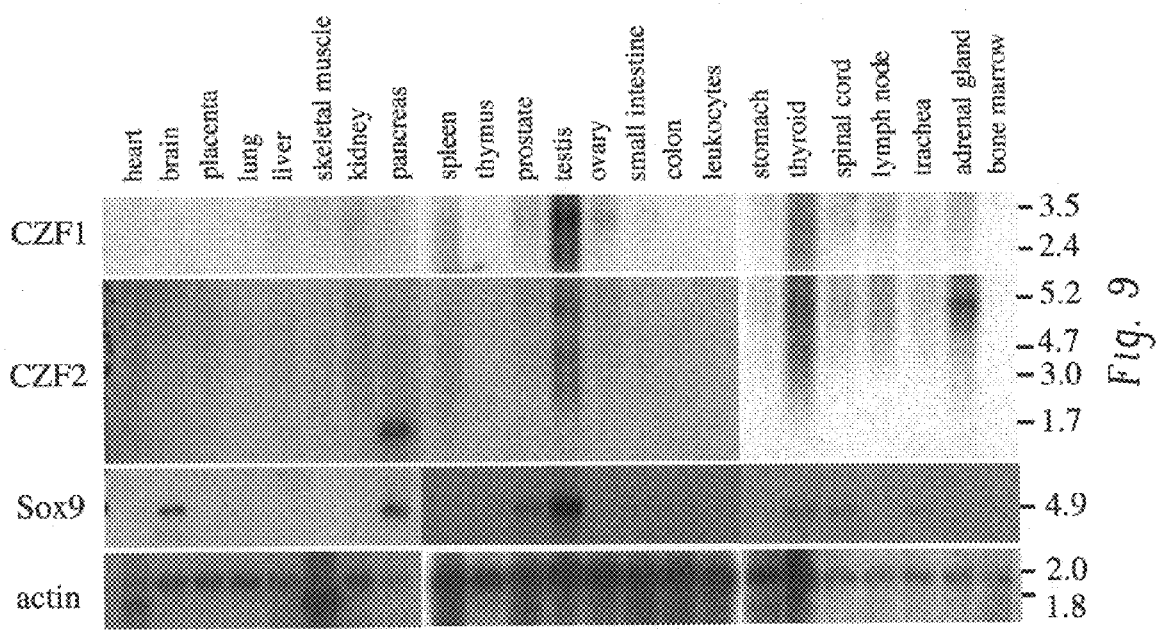
FIG. 9 is a Northern blot analysis of CZF-1, CZF-2 and Sox-9 expression in various tissues of humans.

Expression of both CZF-1 and -2 was examined in multiple tissues obtained from humans (see FIG. 9). Northern blot analysis of CZF-1 showed a restricted pattern of expression, with high mRNA levels in testis and thyroid. Northern blot analysis of CZF-2 showed high level expression in testis, thyroid, adrenal gland and placenta. Since neither of these genes is expressed in all tissues, their function is not required in all cells, and this is consistent with a role in a specialized process such as differentiation.

The expression pattern of both CZF-1 and -2 in the various adult tissues shows overlap with that of Sox-9 (see FIG. 9), which is a transcription factor known to regulate chondrogenesis (see Zhao, et al, 1997, Dev Dyn, 209:377–86 and U.S. Pat. No. 6,143,878), suggesting a functional relationship between Sox-9 and CZF-1 and -2.

Figure 10:
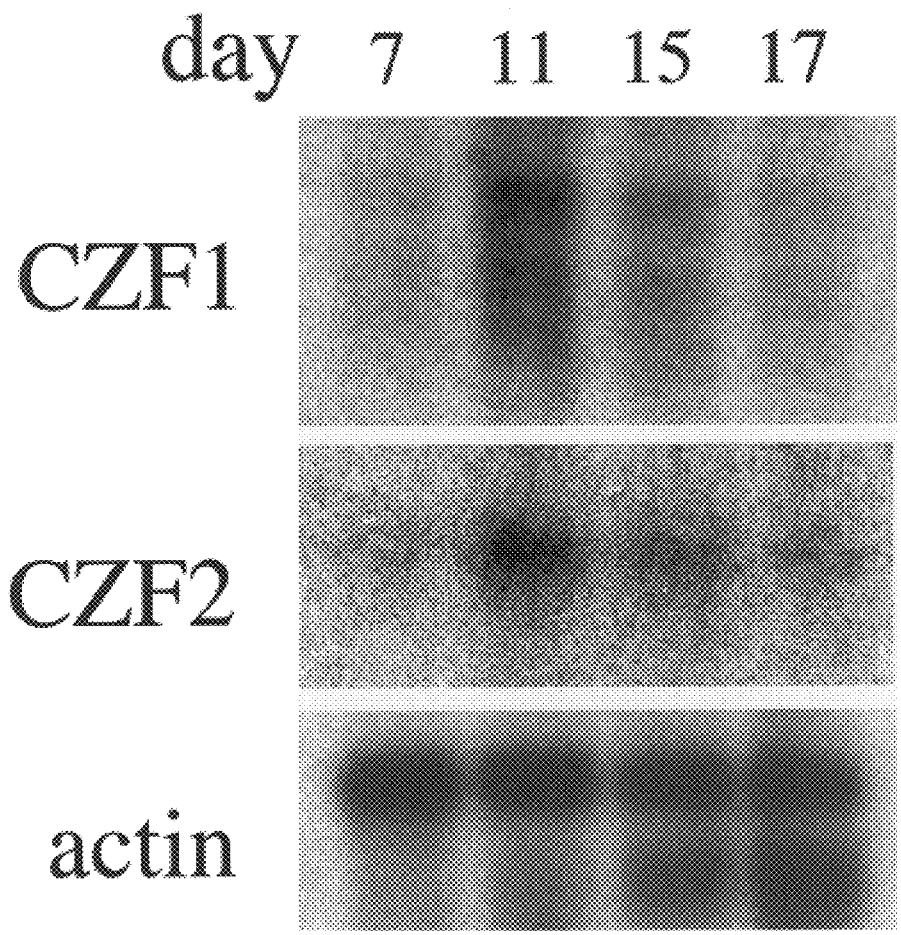
FIG. 10 is a Northern blot analysis of CZF-1 and CZF-2 in developing mouse embryos.

Expression of CZF-1 and -2 was examined in mouse embryonic development using Northern blotting (see FIG. 10). Maximal expression of both the 3.7 kb CZF-1, and the 4.0 kb CZF-2 transcripts was at day 11 and there was little or no expression on day 7. This pattern of expression of CZF-1 during mouse embryo development is very similar to previously published data for Sox-9, a known marker of chondrogenesis.

Figure 11:
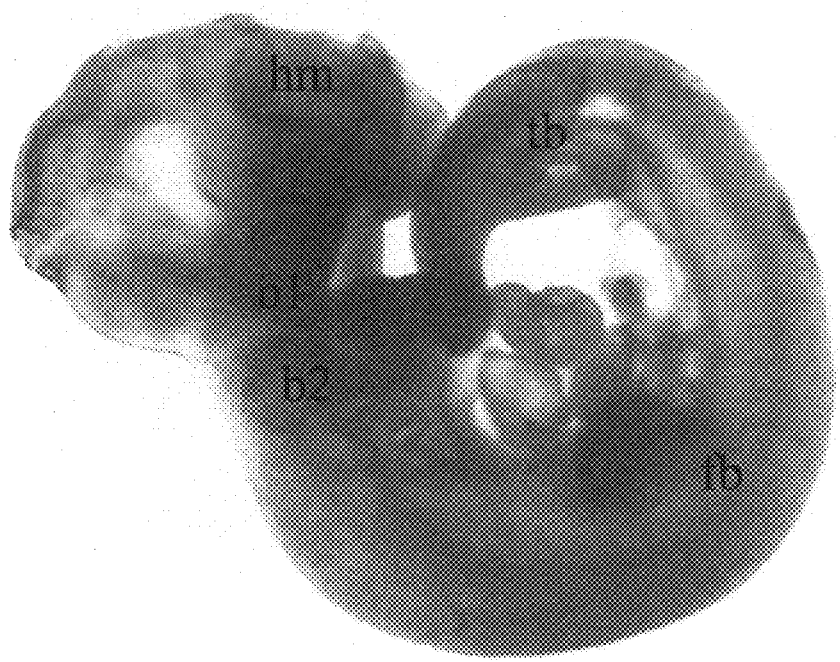
FIG. 11 shows expression of CZF-1 in a 10.5 dpc mouse embryo.

In situ hybridization of CZF-1 to a 10.5 day post-coitus whole mouse embryo (see FIG. 11) shows expression of CZF-1 in head mesenchyme, the first and second brachial arches, the forelimb bud and the tail bud, an expression pattern consistent with involvement of CZF-1 in chondrogenesis.

Isolated Polynucleotides

The present invention provides isolated polynucleotides that comprise the coding sequence of the human CZF-1 gene or a unique fragment thereof. The present invention also provides isolated polynucleotides that comprise the coding sequence of the human CZF-2 gene or a unique fragment thereof. The sequence, SEQ ID NO. 1, of a polynucleotide which comprises the full-length coding sequence of the CZF-1 gene is shown in FIG. 3. The predicted amino acid sequence, SEQ ID NO. 2, of the CZF-1 protein encoded by this polynucleotide is shown in FIG. 4. The sequence, SEQ ID NO. 3, of a polynucleotide which comprises the full-length coding sequence of the CZF-2 gene is shown in FIG. 5. The predicted amino acid sequence, SEQ ID NO. 4, of the CZF-2 protein encoded by this polynucleotide is shown in FIG. 6.

Due to the known degeneracy of the genetic code wherein more than one codon can encode the same amino acid, a DNA sequence may vary from that shown in FIG. 3 and still encode a CZF-1 protein having the amino acid sequence shown in FIG. 4. Similarly, a DNA sequence may vary from that shown in FIG. 5 and still encode a CZF-2 protein whose amino acid sequence is shown in FIG. 6.

The present invention also encompasses polynucleotides having sequences that are capable of hybridizing to the nucleotide sequences of FIGS. 3 and 5 under stringent conditions, preferably highly stringent conditions. Preferably, the isolated polynucleotide comprises a sequence which encodes a protein whose amino acid sequence is at least 90% identical, more preferably 95% identical, to the amino acid sequence of the CZF-1 protein or the CZF-2 protein shown in FIGS. 4 and 6, respectively.

Hybridization conditions are based on the melting temperature TM of the nucleic acid binding complex or probe, as described in Berger and Kimmel (1987) Guide to Molecular Cloning Techniques, Methods in Enzymology, Vol. 152, Academic Press. The term "stringent conditions, as used herein, is the "stringency" which occurs within a range from about $T_m$-5 (5° below the melting temperature of the probe) to about 20° C. below $T_m$. "Highly stringent hybridization conditions" refers to an overnight incubation at 42° C. in a solution comprising 50% formamide, 5×SSC (750 mM NaCl, 75 mM sodium citrate), 50 mM sodium phosphate (pH 7.6), 5×Denhardt's solution, 10% dextran sulfate, and 20 μg/ml denatured, sheared salmon sperm DNA, followed by washing the filters in 0.2×SSC at about 65° C. As recognized in the art, stringency conditions can be attained by varying a number of factors such as the length and nature, i.e., DNA or RNA, of the probe; the length and nature of the target sequence, the concentration of the salts and other components, such as formamide, dextran sulfate, and polyethylene glycol, of the hybridization solution. All of these factors may be varied to generate conditions of stringency which are equivalent to the conditions listed above.

Changes in the stringency of hybridization and signal detection are primarily accomplished through the manipulation of formamide concentration (lower percentages of formamide result in lower stringency); salt conditions, or temperature. For example, moderately high stringency conditions include an overnight incubation at 37° C. in a solution comprising 6×SSPE (20×SSPE=3M NaCl; 0.2 M $NaH_2PO_4$; 0.02M EDTA, pH 7.4), 0.5% SDS, 30% formamide, 100 ug/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC).

Variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

The present invention also encompasses altered polynucleotides which encode a CZF-1 or CZF-2 protein. Such alterations include deletions, additions, or substitutions. Such alterations may produce a silent change and result in a CZF-1 or CZF-2 protein having the same amino acid sequence as the CZF-1 or CZF-2 protein encoded by the unaltered polynucleotide. Such alterations may produce a nucleotide sequence possessing non-naturally occurring codons. For example, codons preferred by a particular prokaryotic or eucaryotic host may be incorporated into the nucleotide sequences shown in FIGS. 3 and 5 to increase the rate of expression of the polypeptides encoded by such sequences. Such alterations, conventionally, are accomplished using site-directed mutagenesis.

In one embodiment of the present invention, isolated polynucleotides comprising the coding sequences of the CZF-1 or CZF-2 genes, as described above, are used as probes to hybridize with RNA extracted from cells or tissues which are suspected of containing chondrocytes. Such cells, for example, can be MPCs that have been grown in culture under conditions where differentiation into chondrocytes will occur.

Such cells can also include MPCs, or MPCs that have partially or entirely differentiated into chondrocytes, that are being prepared for implantation into human subjects that have cartilage defects for the purpose of regenerating a functional cartilage joint surface. Such cells or tissues can also be obtained from human subjects that have previously been implanted with cells that had or are suspected of undergoing chondrogenesis.

The present oligonucleotides and polynucleotides can be used to detect and characterize cells obtained from a tumor that is suspected of being a chondrosarcoma or cells that have characteristics of chondrocytes that may be present in tumor tissue. Such characterization of these cells may reveal whether the tumor cells are undifferentiated mesenchyme, or chondrocytes, for the purpose of choosing appropriate therapy in a patient from which the cells came.

The present oligonucleotides and polynucleotides could also be used to amplify or probe RNA obtained from mesenchymal cells that are being used as screening tools for compounds that are designed to accelerate or retard chondrogenesis. The present oligonucleotides and polynucleotides can be used to monitor the effect of such compounds on this process.

The present oligonucleotides and polynucleotides can also be used to probe histological sections of embryos.

The present oligonucleotides and polynucleotides can also be used to probe a biopsy sample taken from the area in the body where new bone formation is taking place after a fracture. The present oligonucleotides and polynucleotides can also be used to probe cells obtained from any other area of the body where chondrogenesis is suspected of taking place. Examples of other instances where chondrogenesis may occur include formation of osteophytes in a osteoarthritic joint and areas where repair of cartilage defects is occurring by an upwelling of cells from the subchondral bone.

In one example, the CZF-1 or CZF-2 coding sequence is radioactively labeled with $^{32}P$ or digoxigenin, and then hybridized in solution to RNA that is isolated from MPCs that have been grown in culture for 3 days under conditions where differentiation into chondrocytes will occur, as described above, and where the RNA has been separated by size using gel electrophoresis and blotted to nitrocellulose paper. After hybridization and washing of the nitrocellulose paper, hybridization of the CZF-1 or CZF-2 probe to RNA on the nitrocellulose, as revealed by autoradiography, indicates expression of the CZF-1 or CZF-2 genes in the cells or tissues from which the RNA was extracted.

In another embodiment of the present invention, CZF-1 or CZF-2 probes, labeled as described above, are used to hybridize directly to cells or tissues suspected of containing chondrocytes. The cells or tissues are fixed before hybridization, using procedures well known to those skilled in the art. Hybridization is performed under conditions similar to those described above. Detection of hybridization, by autoradiography for example, indicates the presence and location within the cells or tissues where CZF-1 or CZF-2 transcripts are present.

In another embodiment of the present invention, RNA is extracted from cells or tissues suspected of containing chondrocytes and is reverse transcribed into DNA. Then, polynucleotides that contain parts of the nucleotide sequence of the CZF-1 or CZF-2 genes are synthesized and used as primers in a polymerase chain reaction (PCR) to specifically amplify DNA products from the reverse transcription reaction that hybridize to the CZF-1 or CZF-2 primers. DNA products that result from such a PCR reaction indicate that the RNA, which was extracted from cells or tissue, contained mRNAs transcribed from the CZF-1 or CZF-2 genes.

Use of Oligonucleotides and Polynucleotides to Make Proteins

The polynucleotides are also useful for producing CZF-1 and CZF-2 proteins. For example, an RNA molecule encoding a CZF-1 protein is used in a cell-free translation system to prepare such protein. Alternatively, a DNA molecule encoding an CZF-2 protein is introduced into an expression vector and used to transform or transfect cells. Suitable expression vectors include, for example, chromosomal, non-chromosomal and synthetic DNA sequences, e.g., derivatives of SV40, bacterial plasmids, phage DNAs; yeast plasmids, vectors derived from combinations of plasmids and phage DNAs, viral DNA such as vaccinia, adenovirus, fowl pox virus, pseudorabies, baculovirus, and retrovirus. The DNA sequence is introduced into the expression vector by conventional procedures known to those skilled in the art.

Accordingly, the present invention also relates to recombinant constructs comprising one or more of the present polynucleotide sequences. Suitable constructs include, for example, vectors, such as a plasmid, phagemid, or viral vector, into which a sequence that encodes an CZF-1 protein or a CZF-2 protein has been inserted. In the expression vector, the DNA sequence which encodes the CZF-1 or CZF-2 protein is operatively linked to an expression control sequence, i.e., a promoter, which directs mRNA synthesis. Representative examples of such promoters, include the LTR or SV40 promoter, the *E. coli* lac or trp, the phage lambda PL promoter and other promoters known to control expression of genes in prokaryotic or eukaryotic cells or in viruses. The promoter may also be the natural promoter of the CZF-1 or CZF-2 encoding sequence. The expression vector, preferably, also contains a ribosome binding site for translation initiation and a transcription terminator. Preferably, the recombinant expression vectors also include an origin of replication and a selectable marker, such as for example, the ampicillin resistance gene of *E. coli* to permit selection of transformed cells, i.e. cells that are expressing the heterologous DNA sequences. The polynucleotide sequence encoding the CZF-1 or CZF-2 protein is incorporated into the vector in frame with translation initiation and termination sequences.

The polynucleotides encoding an CZF-1 or CZF-2 protein are used to express recombinant protein using techniques well known in the art. Such techniques are described in Sambrook, J. et al (1989) Molecular Cloning A Laboratory Manual, Cold Spring Harbor Press, Plainview, N.Y. and Ausubel, F. M. et al. (1989) Cuurent Protocols in Molecular Biology, John Wile & Sons, New York, N.Y.

Also encompassed by the present invention, are single stranded polynucleotides, hereinafter referred to as antisense polynucleotides, having sequences which are complementary to the DNA and RNA sequences which encode the CZF-1 and CZF-2 proteins. The term complementary as used herein refers to the natural binding of the polynucleotides under permissive salt and temperature conditions by base pairing.

The present invention also encompasses oligonucleotides that are used as primers in polymerase chain reaction (PCR) technologies to amplify transcripts of the genes which encode CZF-1 and CZF-2 proteins or portions of such transcripts. Preferably, the primers comprise 18–30 nucleotides, more preferably 19–25 nucleotides. Preferably, the primers have a G+C content of 40% or greater. Such oligonucleotides are at least 98% complementary with a portion of the DNA strand, i.e., the sense strand, which encodes the respective CZF protein or a portion of its corresponding antisense strand. Preferably, the primer has at least 99% complementarity, more preferably 100% complementarity, with such sense strand or its corresponding antisense strand. Primers which are which have 100% complementarity with the antisense strand of a double-stranded DNA molecule which encodes an CZF protein have a sequence which is identical to a sequence contained within the sense strand. The identity of primers which are 15 nucleotides in length and have full complementarity with a portion of the antisense strand of a double-stranded DNA molecule which encodes the CZF-1 and -2 proteins is determined using the nucleotide sequences, shown in FIGS. 3 and 5.

The present invention also encompasses oligonucleotides that are useful as hybridization probes for isolating and identifying cDNA clones and genomic clones encoding the CZF-1 or CZF-2 protein or allelic forms thereof. Such hybridization probes are also useful for detecting transcripts of the genes which encode the CZF-1 or CZF-2 protein or for mapping of the genes which encode the CZF-1 or CZF-2 proteins. Preferably, such oligonucleotides comprise at least 210 nucleotides, up to 500 nucleotides in length, more preferably at least 230, most preferably from about 210 to 280 nucleotides. Such hybridization probes have a sequence which is at least 90% complementary with a sequence contained within the sense strand of a DNA molecule which encodes an CZF-1 or CZF-2 protein or with a sequence contained within its corresponding antisense strand. Such hybridization probes bind to the sense strand under stringent conditions. The probes are used in Northern assays to detect transcripts of CZF-1 or CZF-2 homologous genes, and in Southern assays to detect CZF-1 or CZF-2 homologous genes. The identity of probes which are 200 nucleotides in length and have full complementarity with a portion of the antisense strand of a double-stranded DNA molecule which encodes the CZF-1 or CZF-2 protein is determined using the nucleotide sequences shown in FIGS. 3 and 5, respectively, and described by the general formula a–b; where a is any integer between 1 and the position number of the nucleotide which is located 200 residues upstream of the 3' end of the sense or antisense strand of the cDNA sequences shown in FIGS. 3 and 5; b is equal to a +200; and where both a and b correspond to the positions of nucleotide residues of the cDNA sequences shown in FIGS. 3 and 5. Tn a preferred embodiment, the oligonucleotide for CZF-1 comprises a sequence which encompasses nucleotide 476 through nucleotide 939 of the sequence shown in FIG. 3. This is the spacer regionbetween the KRAB B domain and the ZF repeats (see FIG. 4). In a preferred embodiment, the oligonucleotide for CZF-2 comprises a sequence which encompasses nucleotide 163 through nucleotide 423 of the sequence shown in FIG. 5. This is the spacer region between the KRAB A domain and the ZF repeats (see FIG. 6).

Such probes or primers are also useful for identifying tissues or cells in which the corresponding CZF gene is expressed. Expression of the CZF-1 or CZF-2 gene in a particular tissue or group of cells is determined using conventional procedures including, but not limited to, Northern analysis, in situ hybridization to RNA or RT-PCR amplification. Isolated polynucleotides encoding a CZF-1 or CZF-2 protein are also useful as chromosome markers to map linked gene positions, to identify chromosomal aberrations such as translocations, inversions and trisomies, to compare with endogenous DNA sequences in patients to identify potential genetic disorders, and as probes to hybridize and thus discover novel, related DNA sequences. For use in such studies and assays, the probes may be labeled with radioisotopes, fluorescent labels, or enzymatic labels. The assays include, but are not limited to, Southern blot, in situ hybridization to DNA in cells and chromosomes, PCR, and allele specific hybridization.

Antibodies

In another aspect, the present invention relates to antibodies which are specific for and bind to the CZF-1 or CZF-2 protein. Such antibodies are useful research tools for identifying tissues that contain normal or elevated levels of the respective protein and for purifying the respective protein from cell or tissue extracts, medium of cultured cells, or partially purified preparations of intracellular and extracellular proteins by affinity chromatography. Such antibodies are also useful for identifying and diagnosing diseases associated with elevated or reduced levels of the CZF-1 or CZF-2 protein. Such antibodies are also useful for monitoring the effect of therapeutic agents on the synthesis of the CZF proteins by cells in vitro and in vivo. Such antibodies may also be employed in procedures, such as co-immunoprecipitation and co-affinity chromatography, for identifying other proteins, activators and inhibitors which bind to the CZF-1 or CZF-2 protein.

The present invention also provides a method for detecting a CZF-1 or CZF-2 protein, in a bodily sample from a patient using antibodies immunospecific for the CZF-1 protein or CZF-2 protein, respectively. The method comprises contacting the antibody with a sample taken from the patient; and assaying for the formation of a complex between the antibody and the corresponding CZF protein present in the sample. The sample may be a tissue or a biological fluid, including but not limited to whole blood, serum, synovial fluid, stool, urine, cerebrospinal fluid, semen, tissue biopsies or excised tissue or cells obtained from swabs and smears. To monitor changes in expression of the CZF protein during fetal development and pregnancy, it is preferred that the sample be amniotic fluid. To monitor changes in expression of the CZF protein during joint disorders, the preferred sample is synovial fluid. To monitor changes in expression of the CZF protein during cancer, the preferred samples is biopsy tissue or blood.

The sample may be untreated, or subjected to precipitation, fractionation, separation, or purification before combining with the anti-CZF protein antibody. For ease of detection, it is preferred that isolated proteins from the sample be attached to a substrate such as a column, plastic dish, matrix, or membrane, preferably nitrocellulose. Preferably, the detection method employs an enzyme-linked immunosorbent assay (ELISA) or a Western immunoblot procedure.

Interactions between an CZF protein in the sample and the corresponding anti-CZF antibody are detected by radiometric, calorimetric, or fluorometric means, size separation, or precipitation. Preferably, detection of the antibody-CZF protein complex is by addition of a secondary antibody that is coupled to a detectable tag, such as for example, an enzyme, fluorophore, or chromophore. Formation of the complex is indicative of the presence of the CZF protein in the test sample. Thus, the method is used to determine whether there is a decrease or increase in the levels of the CZF protein in a test sample as compared to levels of the CZF protein in a control sample and to quantify the amount of the CZF protein in the test sample. Deviation between control and test values establishes the parameters for diagnosing the disease.

Preparing the CZF protein

The present invention relates to novel, isolated, substantially purified, mammalian proteins. As used herein, the term "substantially purified" refers to a protein that is removed from its natural environment, isolated or separated, and at least 60% free, preferably 75% free, and most preferably 90% free from other components with which it is naturally associated.

The novel mammalian proteins are CZF-1 and CZF-2. In one embodiment, the CZF-1 protein is a human protein which comprises amino acids 306–717 of the amino acid sequence set forth in SEQ ID NO. 2. In one embodiment, the CZF-2 protein is a human protein which comprises the amino acid sequence set forth in SEQ ID NO. 4.

CZF-1 is a $Cys_2His_2$-class zinc-finger protein having at its N-terminus, KRAB-A and KRAB-B domains, a spacer region and 16 zinc-finger domains. The molecular mass is 82691.75. CZF-2 is also a $Cys_2His_2$-class zinc-finger protein having at its N-terminus a KRAB A domain, a spacer region, and 12 zinc-finger domains. It has a molecular mass of 59753.89. The KRAB motif is found in numerous zinc finger proteins of this class, and usually indicates that the molecule functions as a transcriptional repressor. The zinc-finger domains act as DNA binding domains, and interact with specific sequences in genomic DNA. As determined using the BLAST software from the National Center for Biotechnology Information, the predicted CZF-1 and CZF-2 proteins show an overall 20–30% similarity to each other, although this may be considerably higher or lower for individual domains as described below.

The CZF-1 and CZF-2 also encompass variants of the CZF proteins shown in FIGS. 4 and 6 respectively. A "variant" as used herein, refers to a protein whose amino acid sequence is similar to one of the amino acid sequences shown in FIGS. 4 and 6, hereinafter referred to as the reference amino acid sequence, but does not have 100% identity with the reference sequence. The variant protein has an altered sequence in which one or more of the amino acids in the reference sequence is deleted or substituted, or one or more amino acids are inserted into the sequence of the reference amino acid sequence. As a result of the alterations, the variant protein has an amino acid sequence which is at least 95% identical to the reference sequence, preferably, at least 97% identical, more preferably at least 98% identical, most preferably at least 99% identical to the reference sequence. Variant sequences which are at least 95% identical have no more than 5 alterations, i.e. any combination of deletions, insertions or substitutions, per 100 amino acids of the reference sequence. Percent identity is determined by comparing the amino acid sequence of the variant with the reference sequence using MEGALIGN project in the DNA STAR program. Sequences are aligned for identity calculations using the method of the software basic local alignment search tool in the BLAST network service (the National Center for Biotechnology Information, Bethesda, Md.) which employs the method of Altschul, S. F., Gish, W., Miller, W., Myers, E. W. & Lipman, D. J. (1990) *J. Mol. Biol.* 215, 403–410. Identities are calculated by the Align program (DNAstar, Inc.) In all cases, internal gaps and amino acid insertions in the candidate sequence as aligned are not ignored when making the identity calculation.

While it is possible to have nonconservative amino acid substitutions, it is preferred that the substitutions be conservative amino acid substitutions, in which the substituted amino acid has similar structural or chemical properties with the corresponding amino acid in the reference sequence. By way of example, conservative amino acid substitutions involve substitution of one aliphatic or hydrophobic amino acids, e.g. alanine, valine, leucine and isoleucine, with another; substitution of one hydroxyl-containing amino acid, e.g. serine and threonine, with another; substitution of one acidic residue, e.g. glutamic acid or aspartic acid, with another; replacement of one amide-containing residue, e.g. asparagine and glutamine, with another; replacement of one aromatic, residue, e.g. phenylalanine and tyrosine, with another; replacement of one basic residue, e.g. lysine, arginine and histidine, with another; and replacement of one small amino acid, e.g., alanine, serine, threonine, methionine, and glycine, with another.

The alterations are designed not to abolish the immunoreactivity of the variant protein with antibodies that bind to the reference protein. Guidance in determining which amino acid residues may be substituted, inserted or deleted without abolishing immunoreactivity of the variant protein with an antibody specific for the respective reference protein are found using computer programs well known in the art, for example, DNASTAR software.

The CZF proteins also encompass fusion proteins comprising an CZF-1 or CZF-2 protein and a tag, i.e., a second protein or one or more amino acids, preferably from about 2 to 65 amino acids, more preferably from about 34 to about 62 amino acids, which are added to the amino terminus of, the carboxy terminus of, or any point within the amino acid sequence of the respective CZF proteins, or a variant of such protein. Typically, such additions are made to stabilize the resulting fusion protein or to simplify purification of an expressed recombinant form of the corresponding CZF protein. Such tags are known in the art. Representative examples of such tags include sequences which encode a series of histidine residues, the epitope tag FLAG, the Herpes simplex glycoprotein D, beta-galactosidase, maltose binding protein, or glutathione S-transferase.

The CZF proteins also encompass CZF-1 or CZF-2 proteins in which one or more amino acids, preferably no more than 10 amino acids, in the respective CZF protein are altered by posttranslation processes or synthetic methods. Examples of such modifications include, but are not limited to, acetylation, amidation, ADP-ribosylation, covalent attachment of flavin, covalent attachment of a heme moiety, covalent attachment of a nucleotide or a lipid, cross-linking gamma-carboxylation, glycosylation, hydroxylation, iodination, methylation, myristoylation, oxidation, pegylation, proteolytic processing, phosphorylation, prenylation, racemization, sulfation, and transfer-RNA mediated additions of amino acids to proteins such as arginylation and ubiquitination.

The CZF protein, may be produced by conventional peptide synthesizers. The CZF protein may also be produced using cell-free translation systems and RNA molecules derived from DNA constructs that the CZF protein. Alternatively, the CZF protein is made by transfecting host cells with expression vectors that comprise a DNA sequence that encodes the respective CZF protein and then inducing expression of the protein in the host cells. For recombinant production, recombinant constructs comprising one or more of the sequences which encode the CZF proteins are introduced into host cells by conventional methods such as calcium phosphate transfection, DEAE-dextran mediated transfection, transvection, microinjection, cationic lipid-mediated transfection, electroporation, transduction, scrape lading, ballistic introduction or infection.

The CZF-1 and CZF-2 proteins may be expressed in suitable host cells, such as for example, mammalian cells, yeast, bacteria, insect cells or other cells under the control of appropriate promoters using conventional techniques. Suitable hosts include, but are not limited to, *E. coli, P. pastoris,* Cos cells and 293 HEK cells. Following transformation of the suitable host strain and growth of the host strain to an appropriate cell density, the cells are harvested by centrifugation, disrupted by physical or chemical means, and the resulting crude extract retained for further purification of the CZF protein.

Conventional procedures for isolating recombinant proteins from transformed host cells, such as isolation by initial extraction from cell pellets or from cell culture medium, followed by salting-out, and one or more chromatography steps, including aqueous ion exchange chromatography, size exclusion chromatography steps, and high performance liquid chromatography (HPLC), and affinity chromatography may be used to isolate the recombinant CZF-1 protein or CZF-2 protein.

Preparation of Antibodies

The CZF proteins thereof are used as immunogens to produce antibodies immunospecific for one or more CZF protein. The term "immunospecific" means the antibodies have substantially greater affinity for the CZF protein than for other proteins. Such antibodies may include, but are not limited to, polyclonal, monoclonal, chimeric, single chain, and Fab fragments.

Antibodies are also prepared using an oligopeptide having a sequence which is identical to a portion of the amino acid sequence of an CZF protein. Preferably the oligopeptide has an amino acid sequence of at least five amino acids, and more preferably, at least 10 amino acids that are identical to a portion of the amino acid sequence of an CZF protein. Such peptides are conventionally fused with those of another protein such as keyhole limpet hemocyanin and antibody produced against the chimeric molecule. Such peptides can be determined using software programs, for example the MacVector program, to determine hydrophilicity and hydrophobicity and ascertain regions of the protein that are likely to be present at the surface of the molecule.

Polyclonal antibodies are generated using conventional techniques by administering the CZF protein or a chimeric molecule to a host animal. Depending on the host species, various adjuvants may be used to increase immunological response. Among adjuvants used in humans, Bacilli-Calmette-Guerin (BCG), and *Corynebacterium parvum,* are especially preferable. Conventional protocols are also used to collect blood from the immunized animals and to isolate the serum and or the IgG fraction from the blood.

For preparation of monoclonal antibodies, conventional hybridoma techniques are used. Such antibodies are produced by continuous cell lines in culture. Suitable techniques for preparing monoclonal antibodies include, but are not limited to, the hybridoma technique, the human B-cell hybridoma technique, and the EBV hybridoma technique.

Various immunoassays may be used for screening to identify antibodies having the desired specificity. These include protocols which. involve competitive binding or immunoradiometric assays and typically involve the measurement of complex formation between the respective CZF protein and the antibody.

Polynucleotides that Encode the CZF-1 and CZF-2 Proteins

Polynucleotides comprising sequences encoding a CZF-1 or CZF-2 protein may be synthesized in whole or in part using chemical methods. Polynucleotides which encode a CZF-1 or CZF-2 protein, particularly alleles of the genes which encode these two proteins, may be obtained by screening a genomic library or cDNA library with a probe comprising sequences identical or complementary to the sequences shown in FIGS. 3 and 5, or with antibodies immunospecific for a CZF-1 or CZF-2 protein to identify clones containing such polynucleotide.

EXAMPLES

The following examples are for purposes of illustration only and are not intended to limit the scope of the invention as defined in the claims which are appended hereto. The references cited in this document are specifically incorporated herein by reference.

Example 1
Growth and Differentiation of Mesenchymal Cells

MSCs were obtained from bone marrow obtained from the iliac crests (hip) of patients undergoing spine surgery. The cells were plated at $10\times10^6$ nucleated cells/100 mm cell culture plate after fractionation on a Percoll gradient. Cells from the gradient that adhered to the culture plate formed colonies that covered about 80–90% of the plate by 14–20 days in monolayer culture. The cells were then trypsinized, counted and $2\times10^5$ cell aliquots were centrifuged at 500×g for 5 minutes in 15 ml polypropylene tubes in 0.5 ml of a defined medium consisting of DMEM-high glucose with ITS+Premix: insulin (6.25 $\mu$g/ml), transferrin (6.25 $\mu$g/ml), selenous acid (6.25 $\mu$g/ml) and linoleic acid (5.35 $\mu$g/ml) with bovine serum albumin (1.25 $\mu$g/ml), and pyruvate (1 mM), ascorbate 2-phosphate (37.5 $\mu$g/ml), dexamethasone ($10^{-7}$ M) and TGF$\beta$-1 (10 ng/ml, recombinant human). The pelleted cells were incubated at 37° C., 5% $CO_2$. Within 24 hours of incubation, the cells formed an aggregate that did not adhere to the walls of the tube. Typically, medium changes were carried out at 2–3 day intervals and aggregates were be harvested at time points up to 21 days. However, cell aggregates were isolated as early as 1 day of culture.

Example 2
Isolation of RNA from Cell Aggregates, Preparation of cDNA Library and Library Screening RNA was prepared from the cells of Example 1 that had been in culture for 3 days, and used to construct a cDNA library in the $\lambda$gt10 vector using standard methods well known to those in the art. This library was screened, using a $^{32}$P-labeled degenerate oligonucleotide probe, coding for the HTGEKP sequence (5'-CA(CT) AC(ACTG) GG(ACTG) GA(AG) AA(AG) CC(ATCG)-3', SEQ ID NO. 5). Cloned cDNA inserts from $\lambda$gt10 clones that hybridized to the oligonucleotide probe were amplified from hybridizing plaques by PCR using LD insert screening amplimers (Clontech) as primers. Inserts were cloned directly into the pCR®2.1 plasmid vector (Invitrogen).

These cloned inserts were then sequenced. Sequence were assembled and analyzed using AssemblyLign and MacVector software (Oxford Molecular Group). CZF-1 was a cDNA of 1485 bp, containing a 412 amino acid residue open reading frame coding for a protein containing 14 zinc-finger domains CZF-2 was a 2166 bp sequence containing a 518 amino acid open reading frame, containing 12 zinc-finger domains.

All of these procedures are well known and routine to one skilled in the art.

Example 3
Characterization of CZF-1 and CZF-2 Clones

The DNA sequences were analyzed using the BLASTX program at NCBI (http://www.ncbi.nlm.nih.gov/). All databases including dbEST, dbSTS, and the non-redundant database were searched.

A BLAST search revealed identity of CZF-1 with sequences within a 3.6 Mb region in 19q13.4, as well as an additional EST isolated from an ovary cDNA library. A BLAST search revealed that the sequence of CZF-2 matched ESTs derived from human bone marrow stromal cells, infant brain and neuro-epithelium cDNA libraries.

Example 4
Expression of CZF-1 and Collagen Types II and X in MPCs Undergoing Chondrogenesis Total cellular RNA was isolated from MPCs that had been grown in culture for different periods (day 0 through day 21 of aggregate culture) under conditions where differentiation to chondrocytes occurred (see Example 1).). Quantitiative PCR was carried out using the Lightcycler instrument and the LightCycler-FastStart DNA Master SYBR Green I kit from Roche.

Example 5
Expression of CZF-1 and -2, and Sox-9 in Multiple Mouse Tissues

Multiple human tissue and mouse embryo developmental stage-specific Northern membranes, purchased from Clontech, were probed with random primer-radiolabelled restriction fragments of the full-length inserts using standard techniques.

Example 6
Characterizing Chondrogenesis in Chick Embryos Using Polynucleotides Derived from CZF-1 or CZF-2 or Anti-CZF-1 or Anti-CZF-2 Antibodies Whole-Mount in Situ Hybridisation on Chicken Embryos (Chitnis et al., 1995; Henrique et al., 1995)

Domingos Henrique and David Ish-Horowicz. (ICRF Dev. Biol. Unit, Oxford; Fax 0865 281310)

Modified from protocols of Ron Conlon (Mt. Sinai, Toronto), Phil Ingham (ICRF Oxford) and David Wilkinson (NIMR, London). Note hybridisation in much reduced salt concentration and omission of RNAse digestion. New conditions for antibody detection are derived from Harland's lab protocol for frogs. Also tried on mouse embryos (7.5–10.5 dpc), and Xenopus embryos, successfully.

Dissections

1. Dissect embryos out in PBS+2 mM EGTA; remove as much of the extra-embryonic membranes as possible.
2. Fix in 10 ml 4% formaldehyde (HCHO) in PBS+2mM EGTA, 1–2 h at room temp; or 4° C., 2 h.
3. Wash three times in PTW (=PBS, 0.1% Tween-20) and once for 1 hour.
4. Transfer to 100% MeOH; can store at this point at −20° C. (less than one month).

Pretreatments and Hybridization

5. Rehydrate embryos through 75%, 50%, 25% MeOH/PTW (allowing embryos to settle), and washing three times with PTW.
6. Treat with 10 $\mu$g/ml proteinase K in PTW for 7 minutes at 37° C. (prewarmed solutions!).
7. Remove proteinase, rinse twice briefly (carefully and quickly!) with PTW, and post-fix for 20 min in 4% HCHO+0.1% Glutaraldehyde, in PTW.
8. Rinse and wash once with PTW.
9. Rinse once with 1:1 PTW/hybridisation mix. Let embryos settle.
10. Rinse with 1 ml hybridisation mix. Let embryos settle.
11. Replace with 1 ml hybridisation mix and incubate with gentle mixing 1 h/65° C. [Can store at −20° C. (before or) after prehybridising.]
12. Add 1 ml pre-warmed hybridisation mix @~1 $\mu$g/ml DIG-labelled RNA probe (possibly 0.1 $\mu$g/ml is enough)
13. Incubate with gentle mixing at 65° C./overnight.

Steps 1–4 are carried out in 15 ml falcon tubes, subsequent steps in 1.7–2 ml in a 2 ml microtube rocking at room temperature unless otherwise stated. Unless otherwise stated, rinses are immediate, and washes are for 5 min.

A stock of 8% glutaradehyde is stored in aliquots at −20° C. Thaw out aliquot just before use.

Hybridization Mix

| Formamide | 50% | 25 ml |
| SSC (20x pH 5 w citric acid!!) | 1.3xSSC | 3.25 ml |
| EDTA (0.5M, pH 8) | 5 mM | 0.5 ml |
| Yeast RNA (20 mg/ml) | 50 µg/ml | 125 µl |
| Tween-20 (10%) | 0.2% | 1 ml |
| CHAPS (10%) | 0.5% | 2.5 ml |
| Heparin (50 mg/ml) | 100 µg/ml | 100 µl |
| $H_2O$ | | 17.5 ml |
| Total | | 50 ml |

Post-Hybridization Washes
1. Rinse twice with prewarmed (65° C.) hybridization mix.
2. Wash 10 min/65° C. with prewarmed hyb mix.
3. Wash 2×30 min/65° C. with Washing solution 1 (50% Formamide/1×SSC/0.1%Tween-20), prewarmed at 65° C.
4. Wash 10 min/65° C. with prewarmed 1:1 Washing solution 1/Maleic Acid Buffer (MABT: 100 mM maleic acid [Sigma M0375], 150 mM NaCl, 0.1% Tween-20, final pH 7.5).
5. Rinse 3 times with MABT.
6. Wash 2×30 min with MABT.
7. Replace with MABT+2% BBR (Boehringer Blocking Reagent [BM 1096 176], make 10% stock in MAB by heating to dissolve, autoclave, aliquot and freeze). Wash for 1 hour at room temp.
8. Preincubate in 2 ml of MABT+2% BBR+20% heat treated goat serum (65° C. for 30 min), for 1–2 hours.
9. Replace with a solution of MABT+2% BBR+20% serum, containing a 1/5000 dilution of anti-DIG-AP antibody (BM 1093 274). Incubate overnight at +4° C.
    After each 70° C. wash, let embryos settle by incubating tube vertically at 70° C., then change supernatants individually so samples don't cool. Keep wash solutions at 70° C. in water-bath.
    Serum is heat-treated at 65° C., 30 min and stored in quick-frozen aliquots at −20° C. Thawed aliquots can be stored at 4° C. with addition of azide to 0.1%.
    If using a probe labelled with UTP-fluorescein, instead of UTP-DIG, use a 1/8000 dilution of the anti-fluorescein-AP antibody (BM 1426 338).

Post-Antibody Washes and Histochemistry
1. Rinse 3 times with MABT. Transfer to scintillation vial.
2. Wash 3×1 h with 10–20 ml MABT, by rolling. If desired, washing without rocking can proceed overnight for lower background.
3. Wash 3×10 min with NTMT.
4. Incubate with 1.5 ml NTMT+4.5 µl/ml NBT+3.5 µl/ml BCIP. Rock for first 20 min. (Develops faster at 37° C., if necessary)
5. When colour has developed to the desired extent (30 min to 3 days), wash 3× with PTW. Refix in 4% HCHO/0.1% Glutaraldehyde/PTW, overnight, followed by PTW washes and storage in PTW/0.1% azide, at +4° C.
6. Clear in 50% glycerol/PTW then 80% glycerol/PTW/0.02% azide.

| NTMT: | 5M NaCl | 1 ml |
| | 2M TrisHCl pH 9.5 | 2.5 ml |
| | 2M $MgCl_2$ | 1.25 ml |
| | 10% Tween-20 | 5 ml |
| | $H_2O$ | 40.25 ml |
| | Total | 50 ml |

Make from stocks on day of use.
N.B. Tween-20 final concentration is 1%.

REFERENCES

Chitnis, A., Henrique, D., Lewis, J., Ish-Horowicz, D., and Kintner, C. (1995). Primary neurogenesis in Xenopus embryos regulated by a homologue of the Drosophila neurogenic gene Delta. Nature 375, 761–766.

Henrique, D., Adam, J., Myat, A., Chitnis, A., Lewis, J., and Ish-Horowicz, D. (1995).

Expression of a Delta homologue in prospective neurons in the chick. Nature 375, 787–790.

Make 20% paraformaldehyde fresh before use: Heat 17 ml of water on a hot plate with stirring. Add 1 drop of 10 N NaOH, then 4 g of paraformaldehyde and stir until dissolved. Make up to 20 ml.

10×PBS (100 ml) 8 g NaCl, 0.2 g KCl, 1.15 g $Na_2HPO_4$, 0.2 g $KH_2PO_4$

Example 7

Hybridization to Sections of Mouse Embryos

Whole mouse sagitally sectioned sections mounted on slides were obtained from day 10.5 post-coitus embryos (obtained from Parogon Biotech, Inc., Baltimore, Md.) and were probed with CZF-1 or Sox-9 cDNAs which had been cloned into a plasmid allowing in vitro transcription. The plasmids were linearized to produce an appropriate blunt or 3'recessed end, and transcribed with T7, T3 or SP6 RNA polymerase to generate digoxigenin-labelled sense and antisense probes using a commercially available kit (Genius 4 system (Boehringer Mannheim, Indianapolis, Ind.).

After digestion with proteinase K, the sections were washed in PBS and fixed in 4% paraformaldehyde-PBS. Digoxigenin-labelled probes were dissolved in hybridization buffer (50% formamide, 10 mM Tris-HCl, pH 7.6, 200 mg/ml yeast tRNA, 1×Denhardt's, 10% dextran sulfate, 600 mM NaCl, 0.25% SDS, 1 mM EDTA, pH 8.0). The hybridization mix was be boiled and applied directly onto sections. After hybridization for 12–16 hrs. at 53° C., the sections were washed in 5×SSC at 56° C. for 1 min, 2×SSC at 56° C. for 30 min, TNE (10 mM TRIS, pH 7.5, 0.5 M NaCl, 1 mM EDTA) at 37° C. for 10 min. Sections were digested with 10 µg/ml RNAse A in TNE at 37° C. for 30 min., followed by washing with TNE at 37° C. for 10 min, 2×SSC at 53° C. for 20 min, and 0.2×SSC at 53° C., twice for 20 min. Sections were blocked using 2% BBR (Boehringer Blocking Reagent) in DIG1 buffer (100 mM Tris-HCl, pH 7.5, 150 mM NaCl). Following a rinse in DIG1 buffer, sections were incubated in a dilution of anti-DIG antibody in DIG1 buffer for 1 hr., washed in DIG1 buffer, and reacted with NTB and X-phos in DIG3 buffer (100 mM Tris pH 9.5, 0.1 M NaCl, 50 mM $MgCl_2$)overnight in the dark. Slides were rinsed in TE buffer and distilled water, counterstained with methyl green and mounted with Permount.

Example 8

Hybridization to Tissue Samples

A tissue sample taken from a human subject that had been previously implanted with chondrocytes or MPCs. Then, biopsy to get cells/tissue from the area. Then hybridization as in Example 7.

What is claimed is:

1. An isolated polynucleotide comprising a coding sequence for a CZF-1 protein or a variant thereof, wherein the CZF-1 protein variant comprises an amino acid sequence at least 90% identical to SEQ ID. NO. 2.

2. The isolated polynucleotide of claim 1 wherein the CZF-1 protein variant comprises a sequence which is at least 95% identical to SEQ ID NO. 2.

3. The isolated polynucleotide of claim 1 wherein the CZF-1 protein variant comprises a sequence which is at least 97% identical to SEQ ID NO. 2.

4. The isolated polynucleotide of claim 2, wherein the CZF-1 protein variant is immunoreactive with an antibody produced by immunizing an animal with a protein comprising the amino acid sequence set forth in SEQ ID NO. 2.

5. The isolated polynucleotide of claim 1, wherein said polynucleotide comprises a sequence which hybridizes under highly stringent conditions to SEQ ID NO. 1.

6. The isolated polynucleotide of claim 1, wherein the CZF-1 protein comprises the amino acid sequence of SEQ ID NO. 2.

* * * * *

SEQUENCE LISTING

<160> NUMBER OF SEQ ID NOS: 13

<210> SEQ ID NO 1
<211> LENGTH: 2666
<212> TYPE: DNA
<213> ORGANISM: Homo sapiens

<400> SEQUENCE: 1

| | | | | | | |
|---|---|---|---|---|---|---|
| aatggagcga | agaccatggg | gactgagtac | acagatgaag | acacagaagc | atagagagga | 60 |
| taagtaatca | ctagcaagtg | gaagaaccgg | gattcagatc | cagaacaggc | tgactccaga | 120 |
| gtcactggct | gtcatgtagt | ttcctcaact | actgcctcag | ctctacaatc | ccagagtaaa | 180 |
| gctcttctcc | aaatgaagag | ccaggaagag | gtagaggtgg | caggaattaa | actttgtaaa | 240 |
| gccatgtccc | tgggttcact | gactttcaca | gatgtggcca | tagacttttc | ccaagatgaa | 300 |
| tgggagtggc | tgaatcttgc | tcagagaagt | ttgtacaaga | aggtgatgtt | agaaaactac | 360 |
| aggaacctag | tttcagtggg | tcttcgcatt | tctaaaccag | atgtgatctc | cttactggag | 420 |
| caagagaaag | acccttgggt | gataaaagga | gggatgaaca | gaggcctgtg | cccagacttg | 480 |
| gagtgtgtgt | gggtgaccaa | atcattatct | ttaaaccagg | atatttatga | agaaaaatta | 540 |
| cccccggcaa | tcataatgga | aagacttaaa | agctatgacc | ttgaatgttc | aacattaggg | 600 |
| aaaaactgga | aatgtgaaga | cttgtttgag | agggagcttg | taaaccagaa | gacacatttt | 660 |
| aggcaagaga | ccatcactca | tatagatact | cttattgaaa | aaagagatca | ctctaacaaa | 720 |
| tctgggacag | tttttcatct | gaatacatta | tcttatataa | aacagatttt | tcccatggaa | 780 |
| gagagaatat | ttaattttca | tacagataag | aaaagcttaa | aaacacattc | agttgtgaaa | 840 |
| aaacacaagc | aagaccgtgg | agaaaagaaa | cttttaaaat | gtaatgactg | tgagaaaata | 900 |
| ttcagcaaaa | tctcaaccct | tactcttcac | caaagaattc | atacaggaga | gaaaccctat | 960 |
| gaatgtattg | aatgtggaaa | ggcctttagc | cagagtgccc | accttgctca | acatcagaga | 1020 |
| atacacacag | gagaaaaacc | ttttgaatgt | actgaatgtg | ggaaagcctt | cagccagaat | 1080 |
| gctcatcttg | ttcaacacca | gagagttcat | actggagaga | aaccttatca | gtgtaagcag | 1140 |
| tgtaataaag | cattcagcca | gcttgcacac | cttgctcaac | atcagagggt | ccacactgga | 1200 |
| gagaaaccct | atgaatgtat | tgaatgtggg | aaggctttta | gtgattgctc | atccctagct | 1260 |
| catcatcgaa | ggattcacac | tgggaaaaga | ccttatgaat | gtattgactg | tgggaaagct | 1320 |
| ttcaggcaga | atgcttctct | tatacgtcat | cggcgatatt | atcatactgg | agagaaaccc | 1380 |
| tttgactgta | ttgattgtgg | gaaggctttc | actgatcaca | taggacttat | tcagcataag | 1440 |
| agaattcata | ctggagagag | accttacaaa | tgtaatgtgt | gtgggaaggc | ttttagccat | 1500 |
| ggctcatctc | tgacagtaca | tcagagaatt | catacaggag | agaaacctta | tgaatgcaat | 1560 |
| atctgtgaga | aagccttcag | ccatcgtggg | tctcttactc | ttcatcagag | agttcatact | 1620 |
| ggagagaaac | cctatgaatg | taagaatgt | gggaaagctt | tccggcagag | cacgcatctg | 1680 |
| gctcatcatc | agagaattca | tactggagag | aaaccttatg | aatgtaagga | atgcagcaaa | 1740 |
| accttcagcc | agaatgcaca | cctcgcgcag | catcagaaaa | tacacactgg | ggagaagcct | 1800 |
| tatgaatgta | aggaacgtgg | taaggccttc | agtcagattg | cacaccttgt | tcagcaccag | 1860 |
| agagttcata | ctggtgagaa | gccttacgaa | tgtattgaat | gtgggaaggc | ctttagtgat | 1920 |
| ggctcatatc | ttgttcaaca | tccgagactc | cacagtggca | aaagaccgta | tgaatgtctt | 1980 |
| gaatgtggga | aggcattcag | gcagagggca | tccttgattt | gtcatcagag | atgtcatact | 2040 |

```
ggtgagaaac cttatgaatg taatgtttgt gggaaagcct ttagccatcg taaatccctt      2100
actctgcatc agagaattca tacaggagag aaaccttatg agtgtaagga atgtagcaaa      2160
gccttcagcc aggttgccca tcttactcta cataagagaa ttcatactgg agaaaggccc      2220
tatgagtgta aagaatgtgg aaaagccttc aggcagagtg tacatcttgc tcatcatcag      2280
cgaattcata ccggagagtc atcagttatt ctctcctctg ccctcccata ccaccaagtc      2340
ctatagattc aatctcgtaa atgcttctag catccatctg ctttttttcca gcacatgtcc      2400 catcatcata gtccaagacg caaccatctc atctggattt ctgcagtagc ataactgttg      2460 cccctttttgc ttctatcaac tacatgttta acactgtagg cagcctaacc ttttaaaaat      2520
aaaaatacat aatttatgtt attttcccat ttaaaacact tgatttgaaa aatatattaa      2580
ctaatccatt tcaaggattt agcacacact ggcatatagt tattgctaaa taaatgctag      2640
ccattaaggt aaaaaaaaaa aaaaaa                                           2666
```

<210> SEQ ID NO 2
<211> LENGTH: 717
<212> TYPE: PRT
<213> ORGANISM: Homo sapiens

<400> SEQUENCE: 2

```
Met Lys Ser Gln Glu Glu Val Glu Val Ala Gly Ile Lys Leu Cys Lys
1               5                   10                  15

Ala Met Ser Gly Ser Leu Thr Phe Thr Asp Val Ala Ile Asp Phe Ser
            20                  25                  30

Gln Asp Glu Trp Glu Trp Leu Asn Leu Ala Gln Arg Ser Leu Tyr Lys
        35                  40                  45

Lys Val Met Leu Glu Asn Tyr Arg Asn Leu Val Ser Val Gly Leu Cys
    50                  55                  60

Ile Ser Lys Pro Asp Val Ile Ser Leu Leu Glu Glu Lys Asp Pro
65                  70                  75                  80

Trp Val Ile Lys Gly Gly Met Asn Arg Gly Leu Cys Pro Asp Leu Glu
                85                  90                  95

Cys Val Trp Val Thr Lys Ser Leu Ser Leu Asn Gln Asp Ile Tyr Glu
            100                 105                 110

Glu Lys Leu Pro Pro Ala Ile Ile Met Glu Arg Leu Lys Ser Tyr Asp
        115                 120                 125

Leu Glu Cys Ser Thr Leu Gly Lys Asn Trp Lys Cys Glu Asp Leu Phe
    130                 135                 140

Glu Arg Glu Leu Val Asn Gln Lys Thr His Phe Arg Gln Glu Thr Ile
145                 150                 155                 160

Thr His Ile Asp Thr Leu Ile Glu Lys Arg Asp His Ser Asn Lys Ser
                165                 170                 175

Gly Thr Val Phe His Leu Asn Thr Leu Ser Tyr Ile Lys Gln Ile Phe
            180                 185                 190

Pro Met Glu Glu Arg Ile Phe Asn Phe His Thr Asp Lys Lys Ser Leu
        195                 200                 205

Lys Thr His Ser Val Val Lys Lys His Lys Gln Asp Arg Gly Glu Lys
    210                 215                 220

Lys Leu Leu Lys Cys Asn Asp Cys Glu Lys Ile Phe Ser Lys Ile Ser
225                 230                 235                 240

Thr Leu Thr Leu His Gln Arg Ile His Thr Gly Glu Lys Pro Tyr Glu
                245                 250                 255
```

-continued

```
Cys Ile Glu Cys Gly Lys Ala Phe Ser Gln Ser Ala His Leu Ala Gln
            260                 265                 270

His Gln Arg Ile His Thr Gly Glu Lys Pro Phe Glu Cys Thr Glu Cys
            275                 280                 285

Gly Lys Phe Ser Gln Asn Ala His Leu Val Gln His Gln Arg Val His
290                 295                 300

Thr Gly Glu Lys Pro Tyr Gln Cys Lys Gln Cys Asn Lys Ala Phe Ser
305                 310                 315                 320

Gln Leu Ala His Leu Ala Gln His Gln Arg Val His Thr Gly Glu Lys
            325                 330                 335

Pro Tyr Glu Leu Ile Glu Cys Gly Lys Ala Phe Ser Asp Cys Ser Ser
            340                 345                 350

Leu Ala His His Arg Arg Ile His Thr Gly Lys Arg Pro Tyr Glu Cys
            355                 360                 365

Ile Asp Cys Gly Lys Ala Phe Arg Gln Asn Ala Ser Leu Ile Arg His
            370                 375                 380

Arg Arg Tyr Tyr His Thr Gly Glu Lys Pro Phe Asp Cys Ile Asp Cys
385                 390                 395                 400

Gly Lys Ala Phe Thr Asp His Ile Gly Leu Ile Gln His Lys Arg Ile
            405                 410                 415

His Thr Gly Glu Arg Pro Tyr Lys Cys Asn Val Cys Gly Lys Ala Phe
            420                 425                 430

Ser His Gly Ser Ser Leu Thr Val His Gln Arg Ile His Thr Gly Glu
            435                 440                 445

Lys Pro Tyr Glu Cys Asn Ile Cys Glu Lys Ala Phe Ser His Arg Gly
            450                 455                 460

Ser Leu Thr Leu His Gln Arg Val His Thr Gly Glu Lys Pro Tyr Glu
465                 470                 475                 480

Cys Lys Glu Cys Gly Lys Ala Phe Arg Gln Ser Thr His Cys Ala His
            485                 490                 495

His Gln Arg Ile His Thr Gly Glu Lys Pro Tyr Glu Cys Lys Glu Cys
            500                 505                 510

Ser Lys Thr Phe Ser Gln Asn Ala His Leu Ala Gln His Gln Lys Ile
            515                 520                 525

His Thr Gly Glu Lys Pro Tyr Glu Cys Lys Glu Arg Gly Lys Ala Phe
            530                 535                 540

Ser Gln Ile Ala His Leu Val Gln His Gln Arg Val His Thr Gly Glu
545                 550                 555                 560

Lys Pro Tyr Glu Cys Ile Glu Cys Gly Lys Ala Phe Ser Asp Gly Ser
            565                 570                 575

Tyr Leu Val Gln His Pro Arg Leu His Ser Gly Lys Arg Pro Tyr Glu
            580                 585                 590

Cys Leu Glu Cys Gly Lys Ala Phe Arg Gln Arg Ala Ser Leu Ile Cys
            595                 600                 605

His Gln Arg Cys His Thr Gly Glu Lys Pro Tyr Glu Cys Asn Val Cys
            610                 615                 620

Gly Lys Ala Phe Ser His Arg Lys Ser Leu Thr Leu His Gln Arg Ile
625                 630                 635                 640

His Thr Gly Glu Lys Pro Tyr Glu Cys Lys Glu Cys Ser Lys Ala Phe
            645                 650                 655

Ser Gln Val Ala His Leu Thr Leu His Lys Arg Ile Gly His Thr Gly
            660                 665                 670

Glu Arg Pro Tyr Glu Cys Lys Glu Cys Gly Lys Ala Phe Arg Glu Gln
```

```
              675                 680                 685
Ser Val His Leu Ala His His Gln Arg Ile His Thr Gly Glu Ser Ser
    690                 695                 700
Val Ile Leu Ser Ser Ala Leu Pro Tyr His Gln Val Leu
705                 710                 715

<210> SEQ ID NO 3
<211> LENGTH: 2143
<212> TYPE: DNA
<213> ORGANISM: Homo sapiens

<400> SEQUENCE: 3
gggagttctt gcaattccag aaccatgact gatgggttgg tgacattcag ggatgtggcc      60
atcgacttct ctcaggagga gtgggaatgc ctggaccctg ctcagaggga cttgtacgtg     120
gatgtaatgt tggagaacta tagtaacttg gtgtcactgg atttggagtc aaaaacgtat     180
gagaccaaaa aaatattttc agaaaatgat atttttgaaa taaattttc ccagtgggag     240
atgaaggaca aaagtaaaac ccttggcctt gaggcatcca tcttcagaaa taattggaag     300
tgcaaaagca tattcgaggg actaaaagga catcaagagg gatacttcag tcaaatgata     360
atcagctatg aaaaaatacc ttcttacaga aaaagtaaat ctcttactcc acatcaaaga     420
attcataata cagagaaatc ctatgttgt aaggaatgtg gaaggcttg cagtcatggc     480
tcaaaacttg ttcaacatga gagaactcat acagctgaaa agcactttga atgtaaagaa     540
tgtgggaaga attatttaag tgcctatcaa ctcaatgtgc atcagagatt tcatactggt     600
gagaaaccct atgagtgtaa ggaatgtggg aagaccttta gctgggatc aagccttgtt     660
aaacatgaga gaattcacac tggtgagaaa ccctatgaat gtaaagaatg tgggaaggcc     720
tttagtcgtg gctatcacct tacccaacat cagaaaattc atattggtgt gaaatcttat     780
aaatgtaagg aatgtgggaa ggccttttt tggggctcaa gccttgctaa acatgagata     840
attcatacag gtgagaaacc ttataaatgt aaagaatgtg gaaggccttt cagtcgtggc     900
tatcaactta ctcagcatca gaaatccat actggtaaga aaccttatga atgtaaaata     960
tgtggaaagg cttttttgttg gggctatcaa cttactcgac atcagatatt tcatactggt    1020
gagaaaccct atgaatgcaa ggaatgtggg aaggcttta attgcggatc aagtcttatt    1080
caacatgaaa gaattcatac tggtgagaaa ccttatgaat gtaaagaatg tggaaaggcc    1140
tttagtcgtg gctatcacct ttctcaacat cagaaaatcc atactggtga aaacctttt    1200
gaatgtaagg aatgtgggaa ggcctttagt tggggttcaa gccttgttaa acatgagaga    1260
gttcatactg tgagaaaatc ccatgaatgt aaagaatgcg aaagacctt ttgtagtggg    1320
tatcaactta ctcgacatca ggtatttcac actggtgaga acccctatga atgtaaggaa    1380
tgtgggaagg cttttaattg tggatcaagc cttgttcaac atgaaagaat ccatacaggg    1440
gagaaaccct atgaatgtaa agaatgtgga aggcttttag tcgtggctat caccttactc    1500
aacatcagaa aattcatacc ggtgagaaac ctttcaaatg taaggaatgt gggaaggcct    1560
tcagttgggg ttcaagccta gttaagcatg agagagtcca tactaatgag aagtcttatg    1620
aatgtaaaga ctgtgggaag gcctttggta gtggctatca acttagtgtt catcagagat    1680
tcatactggg tgagaagctt tatcaacata aggaattcgg gaagaccttt actcgtggct    1740
caaaacttgt tcatgagaga actcatagta atgataaacc ctacaaatat aacgaatgtg    1800
gggaagcctt tctgtggaca acttactcaa atgagaaaat tgatactgat gaaacccttat    1860
gattgaaagt tgtaaaagaa tattttgtgt gtgcgtatag acaacttatc ataataagaa    1920
```

-continued

```
ctcttactct tgagaaacct tgtgaatgta agggttgtgc aaaagccatt catttctgtt      1980
tatgggcaat tatcttgcta tccagcaatt catactagtg agaaatattt tgaatataat      2040
taatatgaaa aggcctttag acttctgtac agtcttattg gatatcaatt tatactgatg      2100
taaaatcatt taaatgaaaa aaaaaaaaaa aaaaaaaaaa aaa                        2143
```

<210> SEQ ID NO 4
<211> LENGTH: 518
<212> TYPE: PRT
<213> ORGANISM: Homo sapiens

<400> SEQUENCE: 4

```
Met Thr Asp Gly Leu Val Thr Phe Arg Asp Val Ala Ile Asp Phe Ser
1               5                   10                  15

Gln Glu Glu Trp Glu Cys Leu Asp Pro Ala Gln Arg Asp Leu Tyr Val
            20                  25                  30

Asp Val Met Leu Glu Asn Tyr Ser Asn Leu Val Ser Leu Asp Leu Glu
        35                  40                  45

Ser Lys Thr Tyr Glu Thr Lys Lys Ile Phe Ser Glu Asn Asp Ile Phe
    50                  55                  60

Glu Ile Asn Phe Ser Gln Trp Glu Met Lys Asp Lys Ser Lys Thr Leu
65                  70                  75                  80

Gly Leu Glu Ala Ser Ile Phe Arg Asn Asn Trp Lys Cys Lys Ser Ile
                85                  90                  95

Phe Glu Gly Leu Lys Gly His Gln Glu Gly Tyr Phe Ser Gln Met Ile
            100                 105                 110

Ile Ser Tyr Glu Lys Ile Pro Ser Tyr Arg Lys Ser Lys Ser Leu Thr
        115                 120                 125

Pro His Gln Arg Ile His Asn Thr Glu Lys Ser Tyr Val Cys Lys Glu
    130                 135                 140

Cys Gly Lys Ala Cys Ser His Gly Ser Lys Leu Val Gln His Glu Arg
145                 150                 155                 160

Thr His Thr Ala Glu Lys His Phe Glu Cys Lys Glu Cys Gly Lys Asn
                165                 170                 175

Tyr Leu Ser Ala Tyr Gln Leu Asn Val His Gln Arg Phe His Thr Gly
            180                 185                 190

Glu Leu Pro Tyr Glu Cys Lys Glu Cys Gly Lys Thr Phe Ser Trp Gly
        195                 200                 205

Ser Ser Leu Val Lys His Glu Arg Ile Gly Thr Gly Glu Lys Pro Tyr
    210                 215                 220

Glu Cys Lys Glu Cys Gly Lys Ala Phe Ser Arg Gly Tyr His Leu Thr
225                 230                 235                 240

Gln His Gln Lys Ile His Ile Gly Val Lys Ser Tyr Lys Cys Lys Glu
                245                 250                 255

Cys Gly Lys Ala Phe Phe Trp Gly Ser Ser Leu Ala Lys His Glu Ile
            260                 265                 270

Ile His Thr Gly Glu Lys Pro Tyr Lys Cys Lys Glu Cys Gly Lys Ala
        275                 280                 285

Arg Ser Arg Gly Tyr Gln Leu Thr Gln His Gln Leu Ile His Thr Gly
    290                 295                 300

Lys Lys Pro Tyr Glu Cys Lys Ile Cys Gly Lys Ala Phe Cys Trp Gly
305                 310                 315                 320

Tyr Gln Leu Thr Arg His Gln Ile Phe His Thr Gly Glu Lys Pro Tyr
                325                 330                 335
```

```
Glu Cys Lys Glu Cys Gly Lys Ala Phe Asn Cys Gly Ser Ser Leu Ile
            340                 345                 350

Gln His Glu Arg Ile His Thr Gly Leu Lys Pro Tyr Glu Cys Lys Glu
        355                 360                 365

Cys Gly Lys Ala Phe Ser Arg Gly Tyr His Leu Ser Gln His Gln Lys
    370                 375                 380

Ile His Thr Gly Glu Lys Pro Phe Glu Cys Lys Cys Gly Lys Ala
385                 390                 395                 400

Phe Ser Trp Gly Ser Ser Leu Val Lys His Glu Arg Val His Thr Gly
                405                 410                 415

Glu Lys Ser His Glu Cys Lys Cys Gly Lys Thr Phe Cys Ser Gly
            420                 425                 430

Tyr Gln Leu Thr Arg His Gln Val Phe His Thr Gly Glu Lys Pro Tyr
        435                 440                 445

Glu Cys Lys Glu Cys Gly Lys Ala Phe Asn Cys Gly Ser Ser Leu Val
    450                 455                 460

Gln His Glu Arg Ile His Thr Gly Glu Lys Pro Tyr Glu Cys Lys Glu
465                 470                 475                 480

Cys Gly Arg Leu Leu Val Val Ala Ile Thr Leu Leu Asn Ile Arg Lys
                485                 490                 495

Phe Ile Pro Val Arg Asn Leu Ser Asn Val Arg Asn Val Gly Arg Pro
                500                 505                 510

Ser Val Gly Val Gln Ala
        515

<210> SEQ ID NO 5
<211> LENGTH: 18
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (1)..(18)
<223> OTHER INFORMATION: n = A, C, T or G

<400> SEQUENCE: 5
cayacnggng araarccn                                                      18

<210> SEQ ID NO 6
<211> LENGTH: 6
<212> TYPE: PRT
<213> ORGANISM: Artificial sequence
<220> FEATURE:
<223> OTHER INFORMATION: Peptide

<400> SEQUENCE: 6

His Thr Gly Glu Lys Pro
1               5

<210> SEQ ID NO 7
<211> LENGTH: 4
<212> TYPE: PRT
<213> ORGANISM: Artificial sequence
<220> FEATURE:
<223> OTHER INFORMATION: Peptide

<400> SEQUENCE: 7

Cys Cys His His
1
```

<210> SEQ ID NO 8
<211> LENGTH: 44
<212> TYPE: PRT
<213> ORGANISM: Artificial sequence
<220> FEATURE:
<223> OTHER INFORMATION: Peptide
<220> FEATURE:
<221> NAME/KEY: misc_feature
<222> LOCATION: (1)..(44)
<223> OTHER INFORMATION: X = R, H, I, K, M, F, T, W or V

<400> SEQUENCE: 8

Tyr Xaa Cys Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Cys Xaa Xaa Xaa Phe
            20                  25                  30

Xaa Xaa Xaa Xaa Xaa Leu Xaa Xaa His Xaa Xaa Xaa
        35                  40

<210> SEQ ID NO 9
<211> LENGTH: 45
<212> TYPE: PRT
<213> ORGANISM: Artificial sequence
<220> FEATURE:
<223> OTHER INFORMATION: Peptide
<220> FEATURE:
<221> NAME/KEY: misc_feature
<222> LOCATION: (1)..(45)
<223> OTHER INFORMATION: X = R, H, I, K, M, F, T, W or V

<400> SEQUENCE: 9

Tyr Xaa Cys Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Cys Xaa Xaa Xaa Phe
            20                  25                  30

Xaa Xaa Xaa Xaa Xaa Leu Xaa Xaa His Xaa Xaa Xaa Xaa
        35                  40                  45

<210> SEQ ID NO 10
<211> LENGTH: 46
<212> TYPE: PRT
<213> ORGANISM: Artificial sequence
<220> FEATURE:
<223> OTHER INFORMATION: Peptide
<220> FEATURE:
<221> NAME/KEY: misc_feature
<222> LOCATION: (1)..(46)
<223> OTHER INFORMATION: X = R, H, I, K, M, F, T, W or V

<400> SEQUENCE: 10

Tyr Xaa Cys Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Cys Xaa Xaa Xaa Phe
            20                  25                  30

Xaa Xaa Xaa Xaa Xaa Leu Xaa Xaa His Xaa Xaa Xaa Xaa Xaa
        35                  40                  45

<210> SEQ ID NO 11
<211> LENGTH: 44
<212> TYPE: PRT
<213> ORGANISM: Artificial sequence
<220> FEATURE:
<223> OTHER INFORMATION: Peptide
<220> FEATURE:
<221> NAME/KEY: misc_feature
<222> LOCATION: (1)..(44)

```
<223> OTHER INFORMATION: X = R, H, I, K, M, F, T, W or V

<400> SEQUENCE: 11

Phe Xaa Cys Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Cys Xaa Xaa Xaa Phe
                20                  25                  30

Xaa Xaa Xaa Xaa Xaa Leu Xaa Xaa His Xaa Xaa Xaa
            35                  40

<210> SEQ ID NO 12
<211> LENGTH: 45
<212> TYPE: PRT
<213> ORGANISM: Artificial sequence
<220> FEATURE:
<223> OTHER INFORMATION: Peptide
<220> FEATURE:
<221> NAME/KEY: misc_feature
<222> LOCATION: (1)..(45)
<223> OTHER INFORMATION: X = R, H, I, K, M, F, T, W or V

<400> SEQUENCE: 12

Phe Xaa Cys Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Cys Xaa Xaa Xaa Phe
                20                  25                  30

Xaa Xaa Xaa Xaa Xaa Leu Xaa Xaa His Xaa Xaa Xaa Xaa
            35                  40                  45

<210> SEQ ID NO 13
<211> LENGTH: 46
<212> TYPE: PRT
<213> ORGANISM: Artificial sequence
<220> FEATURE:
<223> OTHER INFORMATION: Peptide
<220> FEATURE:
<221> NAME/KEY: misc_feature
<222> LOCATION: (1)..(46)
<223> OTHER INFORMATION: X = R, H, I, K, M, F, T, W or V

<400> SEQUENCE: 13

Phe Xaa Cys Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Cys Xaa Xaa Xaa Phe
                20                  25                  30

Xaa Xaa Xaa Xaa Xaa Leu Xaa Xaa His Xaa Xaa Xaa Xaa
            35                  40                  45
```